US006998253B1

(12) United States Patent
Presta et al.

(10) Patent No.: US 6,998,253 B1
(45) Date of Patent: Feb. 14, 2006

(54) ALTERED POLYPEPTIDES WITH INCREASED HALF-LIFE

(75) Inventors: Leonard G. Presta, San Francisco, CA (US); Bradley R. Snedecor, Portola Valley, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 09/628,568

(22) Filed: Jul. 31, 2000

Related U.S. Application Data

(63) Continuation of application No. 08/422,112, filed on Apr. 14, 1995, now Pat. No. 6,121,022.

(51) Int. Cl.
  C07H 21/00 (2006.01)
  C12N 5/10 (2006.01)
(52) U.S. Cl. .................... 435/69.1; 435/69.3; 435/69.6; 435/243; 435/320.1; 435/325; 435/410; 536/23.4; 536/23.53
(58) Field of Classification Search ............... 536/23.4, 536/23.53; 424/133.1, 134.1; 530/387.3; 435/69.1, 69.3, 69.6, 320.1, 243, 410, 325
See application file for complete search history.

(56) References Cited

U.S. PATENT DOCUMENTS

| 5,475,091 A | 12/1995 | Springer et al. |
| 5,489,533 A | 2/1996 | Springer et al. |
| 6,096,871 A * | 8/2000 | Presta et al. ............. 530/387.3 |
| 6,121,022 A * | 9/2000 | Presta et al. ............... 435/69.7 |

FOREIGN PATENT DOCUMENTS

| EP | 0 239 400 | 9/1987 |
| WO | WO 93/22332 | 11/1993 |
| WO | WO 94/04689 | 11/1994 |

OTHER PUBLICATIONS

Diegel, M.L. et al., "Regulation of HIV Production by Blood Mononuclear Cells from HIV-Infected Donors: II. HIV-1 Production Depends on T-Cell-Monocyte Interaction," AIDS Research and Human Retroviruses, 9(5):465-473 (1993).
Batra, J.K. et al., "Insertion of constant Region Domains of Human IgG.sub.1 Into CD4-PE40 Increases Its Plasma Half-Life," Molecular Immunology, 30(4):379-386 (1993).
Kim, J.-K. et al., "Catabolism of the Murine IgG1 Molecule: Evidence that Both CH2-CH3 Domain Interfaces are Required for Persistence of IgG1 in the Ciruculation of Mice," Scand. J. Immunol., 40:457-465 (1994).
Traunecker et al., "Bispecific single chain molecules (Janusins) target cytotoxic lymphocytes on HIV infected cells," EMBO J. 10(12): 3655-3659 (1991).

Brambell, "The Transmission of Immunity from Mother to Young and the Catabolism of Immunoglobulins" Lancet pp. 1087-1093 (Nov. 19, 1966).
Brambell et al., "A Theoretical Model of .gamma.-Globulin Catabolism" Nature 203:1352-1355 (1964).
Deisenhofer, "Crystallographic Refinement and Atomic Models of a Human Fc fragment and Its Complex with Fragment B of Protein A from *Staphylococcus aureus* at 2.9- and 2.8-A Resolution" Biochemistry 20(9):2361-2370 (1981).
Dima et al., "Effect of protein A and its fragment B on the catabolic and Fc receptor sites of IgG" European Journal of Immunology 13:605-614 (1983).
Ellerson et al., "Isolation and Characterization of a Fragment Corresponding to the C.gamma. Homology Region of Human Immunoglobin G.sup.1." Journal of Immunology 116 (2):510-517 (Feb. 1976).
Kim et al., "Identifying amino acid residues that influence plasma clearance of murine IgGa fragments by site-directed mutagenesis" European Journal of Immunology 24:542-548 (1994).
Knauff et al., "Relationship of Effective Molecular Size to Systematic Clearance in Rats of Recombinant Interleukin-2 Chemically Modified with Water-soluable Polymers" Journal of Biological Chemistry 263:15064-15070 (1988).
Masson, "Elimination of Infectious Antigens and Increase of IgG Catabolism as Possible Modes of Action of IVIg" Journal of Autoimmunity 6:683-689 (1993).
Nose et al., "Biological significance of carbohydrate chains on monoclonal antibodies" Proc. Natl. Acad. Sci. USA 80:6632-6636 (Nov. 1983).
Pollock et al., "Intravascular metabolism of normal and mutant mouse immunoglobulin molecules" European Journal of Immunology 20:2021-2027 (1990).
Spector, "The reabsorption of labelled proteins by the normal and nephrotic rat kidneu" J. Path. Bact. 68:187-196 (1954).
Spiegelberg, "Biological Activities of Immunoglobulins of Different Classes and Subclasses" Advances in Immunology 19:259-294 (1974).
Spiegelberg et al., "The Catabolism of Homologous and Heterologous 75 Gamma Globulin Fragments" J. of Experimental Medicine. Dubos et al. vol. 121(1):323-338 (1965).
Tao et al., "Role of Carbohydrate in the Structure and Effector Functions Mediated by the Human IgG Constant Region" Journal of Immunology 143(8):2595-2601 (Oct. 15, 1989).

(Continued)

Primary Examiner—David Saunders
(74) Attorney, Agent, or Firm—Merchant & Gould P.C.

(57) ABSTRACT

Polypeptides that are cleared from the kidney and do not contain in their original form a Fc region of an IgG are altered so as to comprise a salvage receptor binding epitope of an Fc region of an IgG and thereby have increased circulatory half-life.

11 Claims, 3 Drawing Sheets

OTHER PUBLICATIONS

Waldmann et al.. "Catabolism of Immunoglobulins" Progress in Immunology 1:1187-1191 (1971).

Wawrzynczak et al., "Blood Clearance in the Rat of a Recombinant Mouse Monoclonal Antibody Lacking the N-Linked Oligosaccharide Side Chains of the $C_H2$ Domains" Molecular Immunology 29(2):213-220.

Wawrynczak et al., "Recombinant Mouse Monoclonal Antibodies with single Amino Acid SubstitutionsAffecting C1q and High Affinity Fc Receptor Binding Have Identical Serum Half-lives in the BALB/c Mouse" Molecular Immunology 29(2):221-227 (1992).

Wochner et al., "The Role of the Kidney in the Catabolism of Bence Jones Proteins and Immunoglobulin Fragments" Journal of Experimental Medicine 126(2):207-221 (Aug. 1, 1967).

Yasmeen et al., "The Distribution of effector Functions Among the $C_{\gamma}2$ and $C_{\gamma}3$ Homology Region Immunoglobulin $G^1$" Journal of Immunology 116(2): 518-526 (Feb. 1976).

Zuckier et al., "Immunologic and Pharmacologic Concepts of Monoclonal Antibodies" Seminars in Nuclear Medicine 19(3):166-186 (Jul. 1989).

Zuckier et al., "The Use of Severe Combined Immunodeficiency Mice to Study the Metabolism of Human Immunoglobulin G" Cancer Supplement 73(3):794-799 (Feb. 1, 1994).

Archelos, J. et al., "Inhibition of Experimental Autoimmune Neuritis by an Antibody to the Lymphocyte Function-Associated Antigen-1," *Laboratory Investigation*, vol. 70, No. 5, pp. 667-675 (May 1994).

Connolly, M. et al., "Treatment of Murine Lupus with Monoclonal Antibodies to Lymphocyte Function-Associated Antigen-1: Dose-Dependent Inhibition of Autoantibody Production and Blockade of the Immune Response to Therapy," *Clinical Immunology and Immunopathology*, vol. 72, No. 2, pp. 198-203 (Aug. 1994).

Hasegawa, Y. et al., "Prevention of autoimmune insulin-dependent diabetes in non-obese diabetic mice by anti-LFA-1 and anti-ICAM-1 mAb," *International Immunology*, vol. 6, No. 6, pp. 831-838 (1994).

Herold, K. et al., "Prevention of Autoimmune Diabetes by Treatment with Anti-LFA-1 and Anti-ICAM-1 Monoclonal Antibodies," *Cellular Immunology*, vol. 157, No. 2, pp. 489-500 (Sep. 1994).

Kawamura, O., "Antinephritic effect of anti-ICAM-1 monoclonal antibody and anti-LFA-1 monoclonal antibody on accelerated-type anti-GBM nephritis in rats," *The Japanese Journal of Nephrology*, vol. 36, No. 2, pp. 103-112 (Feb. 1994)— Abstract Only, in English.

Laberge, S. et al., "Role of VLA-4 and LFA-1 in Allergen-induced Airway Hyperresponsiveness and Lung Inflammation in the Rat," *American Journal of Respiratory and Critical Care Medicine*, vol. 151, No. 3, pp. 822-829 (Mar. 1995).

Matsuo, Y. et al., "Role of cell adhesion molecules in brain injury after transient middle cerebral artery occlusion in the rat," *Brain Research*, vol. 656, No. 2, pp. 344-352, (Sep. 12, 1994).

Nakao, Y. et al., "Monoclonal Antibodies Against ICAM-1 and LFA-1 Prolong Nerve Allograft Survival," *Muscle & Nerve*, vol. 18, No. 1, pp. 93-102 (Jan. 1995).

Tamiya, Y. et al., "Protective effect of monoclonal antibodies against LFA-1 and ICAM-1 on myocardial reperfusion injury following global ischemia in rat hearts," *Immunopharmacology*, vol. 29, No. 1 pp. 53-63 (Feb. 1995).

Tanaka, Y. et al., "Inhibition of Inflammatory Liver Injury by a Monoclonal Antibody against Lymphocyte Function-Associated Antigen-1," *The Journal of Immunology*, vol. 151, No. 9, pp. 5088-5095 (Nov. 1, 1993).

Uchio, E. et al., "Suppression of Experimental Uveitis With Monoclonal Antibodies to ICAM-1 and LFA-1," *Investigative Ophthalmology & Visual Science*, vol. 35, No. 5, pp. 2626-2631 (Apr. 1994).

Zahalka, M. et al., "Blocking Lymphoma Invasiveness with a Monoclonal Antibody Directed against the β-Chain of the Leukocyte Adhesion Molecule (CD18)," *The Journal of Immunology*, vol. 150, No. 10. pp. 4466-4477 (May 15, 1993).

* cited by examiner

| | |
|---|---|
| hIgG1 | Sequence of human IgG1 CH1 domain |
| hIgG2 | Sequence of human IgG2 CH1 domain |
| hIgG3 | Sequence of human IgG3 CH1 domain |
| hIgG4 | Sequence of human IgG4 CH1 domain |
| humK | Sequence of human kappa CL domain |
| humL | Sequence of human lambda CL domain |

```
                  114                       128                 139
                   ↓                         ↓                   ↓
hIgG1       A S T K G P S V F P L A P S S K S T S G G T A A L
hIgG2       A S T K G P S V F P L A P C S R S T S E S T A A L
hIgG3       A S T K G P S V F P L A P C S R S T S G G T A A L
hIgG4       A S T K G P S V F P L A P C S R S T S E S T A A L 108                       122                 131
                   ↓                         ↓                   ↓
humK        R T V A A P S V F I F P P S D E Q L K S G T A S V
humL        Q P K A A P S V T L F P P S S E E L Q A N K A T L
            -----------------------------------------------------
FabCABv1b   A S T K G P S V F P L A P S P K N S S M I S N T P A L
of interest                             P K N S S M I S N T P most important                                      * * *   * hIgG1        G C L V K D Y F P E P V T V S W N S G A L T S
hIgG2        G C L V K D Y F P E P V T V S W N S G A L T S
hIgG3        G C L V K D Y F P E P V T V S W N S G A L T S
hIgG4        G C L V K D Y F P E P V T V S W N S G A L T S humK         V C L L N N F Y P R E A K V Q W K V D N A L Q
humL         V C L I S D F Y P G A V T V A W K A D S S P V
             -----------------------------------------------------
FabCABv1b    G C L V K D Y F P E P V T V S W N S G A L T S hIgG1        G V H T F P A V L Q S S G - - - L Y S L S S V
hIgG2        G V H T F P A V L Q S S G - - - L Y S L S S V
```

FIG. 2a

```
hIgG3      G V H T F P A V L Q S S G - - - L Y S L S S V
hIgG4      G V H T F P A V L Q S S G - - - L Y S L S S V
humK        S G N S Q E S V T E Q D S K D S T Y S L S S T
humL        K A G V E T T T P S K Q S N N - K Y A A S S Y
           ------------------------------------------------
FabCABv1b  G V H T F P A V L Q S S G - - - L Y S L S S V
```

```
                  193             200 203
                   ↓               ↓   ↓
hIgG1       V T V P S S S L G T - Q T Y I C N V N H K P S
hIgG2       V T V P S S N F G T - Q T Y T C N V D H K P S
hIgG3       V T V P S S S L G T - Q T Y T C N V-N H K P S
hIgG4       V T V P S S S L G T - K T Y T C N V D H K P S
                        181               190
                         ↓                 ↓
humK        L T L S K A D Y E K H K V Y A C E V T H Q G L
humL        L S L T P E Q W K S H R S Y S C Q V T H E G S
            ------------------------------------------------
FabCABv1b   V T V P H Q S L G T - Q T Y I C N V N H K P S
of interest         H Q N L S D G K most important      * * *       *   *
```

```
hIgG1      N T K V D K R V - - -
hIgG2      N T K V D K T V - - -
hIgG3      N T K V D K R V - - -
hIgG4      N T K V D K R V - - - humK       S S P V T K S F N R G E C
humL       T V E K T V A P T E C S
           ------------------------------------
FabCABv1b  N T K V D K R V - - -
```

FIG. 2b

SEQUENCE LISTING

<160> NUMBER OF SEQ ID NOS: 31

<210> SEQ ID NO 1
<211> LENGTH: 8
<212> TYPE: PRT
<213> ORGANISM: Artificial Sequence
<220> FEATURE:
<223> OTHER INFORMATION: Sequence comprising a salvage receptor binding

```
                               epitope

<400> SEQUENCE: 1

His Gln Asn Leu Ser Asp Gly Lys
 1               5

<210> SEQ ID NO 2
<211> LENGTH: 8
<212> TYPE: PRT
<213> ORGANISM: Artificial Sequence
<220> FEATURE:
<223> OTHER INFORMATION: Sequence comprising a salvage receptor binding
      epitope

<400> SEQUENCE: 2

His Gln Asn Ile Ser Asp Gly Lys
 1               5

<210> SEQ ID NO 3
<211> LENGTH: 11
<212> TYPE: PRT
<213> ORGANISM: Artificial Sequence
<220> FEATURE:
<223> OTHER INFORMATION: Sequence comprising a salvage receptor binding
      epitope

<400> SEQUENCE: 3

Pro Lys Asn Ser Ser Met Ile Ser Asn Thr Pro
 1               5                  10

<210> SEQ ID NO 4
<211> LENGTH: 98
<212> TYPE: PRT
<213> ORGANISM: Homo sapiens

<400> SEQUENCE: 4

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 5
<211> LENGTH: 98
<212> TYPE: PRT
<213> ORGANISM: Homo sapiens

<400> SEQUENCE: 5

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45
```

-continued

```
Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val

<210> SEQ ID NO 6
<211> LENGTH: 98
<212> TYPE: PRT
<213> ORGANISM: Homo sapiens

<400> SEQUENCE: 6

Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val

<210> SEQ ID NO 7
<211> LENGTH: 98
<212> TYPE: PRT
<213> ORGANISM: Homo sapiens

<400> SEQUENCE: 7

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val

<210> SEQ ID NO 8
<211> LENGTH: 107
<212> TYPE: PRT
<213> ORGANISM: Homo sapiens

<400> SEQUENCE: 8

Arg Thr Val Ala Ala Pro Ser Val Phe Ile Phe Pro Pro Ser Asp Glu
 1               5                  10                  15
```

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 9
<211> LENGTH: 105
<212> TYPE: PRT
<213> ORGANISM: Homo sapiens

<400> SEQUENCE: 9

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Pro Ser Lys Gln Ser Asn Asn Lys
        50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 10
<211> LENGTH: 100
<212> TYPE: PRT
<213> ORGANISM: Artificial Sequence
<220> FEATURE:
<223> OTHER INFORMATION: Humanized Fab v1b variant

<400> SEQUENCE: 10

Ala Ser Thr Lys Gly Pro Ser Val Phe Pro Leu Ala Pro Ser Pro Lys
1               5                   10                  15

Asn Ser Ser Met Ile Ser Asn Thr Pro Ala Leu Gly Cys Leu Val Lys
                20                  25                  30

Asp Tyr Phe Pro Glu Pro Val Thr Val Ser Trp Asn Ser Gly Ala Leu
            35                  40                  45

Thr Ser Gly Val His Thr Phe Pro Ala Val Leu Gln Ser Ser Gly Leu
        50                  55                  60

Tyr Ser Leu Ser Ser Val Val Thr Val Pro His Gln Ser Leu Gly Thr
65                  70                  75                  80

Gln Thr Tyr Ile Cys Asn Val Asn His Lys Pro Ser Asn Thr Lys Val
                85                  90                  95

Asp Lys Arg Val
            100

```
<210> SEQ ID NO 11
<211> LENGTH: 7
<212> TYPE: PRT
<213> ORGANISM: Artificial Sequence
<220> FEATURE:
<223> OTHER INFORMATION: Sequence comprising a salvage receptor binding
      epitope

<400> SEQUENCE: 11

His Gln Ser Leu Gly Thr Gln
1               5

<210> SEQ ID NO 12
<211> LENGTH: 29
<212> TYPE: DNA
<213> ORGANISM: Artificial Sequence
<220> FEATURE:
<223> OTHER INFORMATION: Oligonucleotide

<400> SEQUENCE: 12
gtgaccgtgc ctcaccagag cttgggcac                                    29

<210> SEQ ID NO 13
<211> LENGTH: 53
<212> TYPE: DNA
<213> ORGANISM: Artificial Sequence
<220> FEATURE:
<223> OTHER INFORMATION: Oligonucleotide

<400> SEQUENCE: 13
tggcaccctc ccctaagaac tcgagcatga tcagcaacac accggccctg ggc          53

<210> SEQ ID NO 14
<211> LENGTH: 11
<212> TYPE: PRT
<213> ORGANISM: Artificial Sequence
<220> FEATURE:
<223> OTHER INFORMATION: Constant region sequence

<400> SEQUENCE: 14

Ser Ser Lys Ser Thr Ser Gly Gly Thr Ala Ala
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Sequence comprising a salvage receptor binding
      epitope

<400> SEQUENCE: 15

Ser Pro Lys Asn Ser Ser Met Ile Ser Asn Thr Pro Ala
1               5                   10

<210> SEQ ID NO 16
<211> LENGTH: 34
<212> TYPE: DNA
<213> ORGANISM: Artificial Sequence
<220> FEATURE:
<223> OTHER INFORMATION: Oligonucleotide

<400> SEQUENCE: 16
tggcaccctc caaatcgagc atcacagcgg ccct                              34

<210> SEQ ID NO 17
<211> LENGTH: 9
```

```
<212> TYPE: PRT
<213> ORGANISM: Artificial Sequence
<220> FEATURE:
<223> OTHER INFORMATION: Constant region sequence

<400> SEQUENCE: 17

Ser Ser Lys Ser Thr Ser Gly Gly Thr
1               5

<210> SEQ ID NO 18
<211> LENGTH: 6
<212> TYPE: PRT
<213> ORGANISM: Artificial Sequence
<220> FEATURE:
<223> OTHER INFORMATION: Constant region sequence

<400> SEQUENCE: 18

Ser Lys Ser Ser Ile Thr
1               5

<210> SEQ ID NO 19
<211> LENGTH: 44
<212> TYPE: DNA
<213> ORGANISM: Artificial Sequence
<220> FEATURE:
<223> OTHER INFORMATION: Oligonucleotide

<400> SEQUENCE: 19
tggtgaccgt gatctcgagc cacttgggcc agcagaccta catc                    44

<210> SEQ ID NO 20
<211> LENGTH: 9
<212> TYPE: PRT
<213> ORGANISM: Artificial Sequence
<220> FEATURE:
<223> OTHER INFORMATION: Constant region sequence

<400> SEQUENCE: 20

Val Pro Ser Ser Ser Leu Gly Thr Gln
1               5

<210> SEQ ID NO 21
<211> LENGTH: 9
<212> TYPE: PRT
<213> ORGANISM: Artificial Sequence
<220> FEATURE:
<223> OTHER INFORMATION: Sequence comprising a salvage receptor binding
      epitope

<400> SEQUENCE: 21

Val Ile Ser Ser His Leu Gly Gln Gln
1               5

<210> SEQ ID NO 22
<211> LENGTH: 45
<212> TYPE: PRT
<213> ORGANISM: Artificial Sequence
<220> FEATURE:
<223> OTHER INFORMATION: Hinge region sequence including a Leucine
      Zipper

<400> SEQUENCE: 22

Cys Pro Pro Cys Pro Ala Pro Glu Leu Leu Gly Gly Arg Met Lys Gln
1               5                   10                  15

Leu Glu Asp Lys Val Glu Glu Leu Leu Ser Lys Asn Tyr His Leu Glu
                20                  25                  30
```

```
Asn Glu Val Ala Arg Leu Lys Lys Leu Val Gly Glu Arg
        35                  40                  45
```

<210> SEQ ID NO 23
<211> LENGTH: 28
<212> TYPE: DNA
<213> ORGANISM: Artificial Sequence
<220> FEATURE:
<223> OTHER INFORMATION: Oligonucleotide

<400> SEQUENCE: 23
tcgagcatga tctctagaac accggccc                                     28

<210> SEQ ID NO 24
<211> LENGTH: 36
<212> TYPE: DNA
<213> ORGANISM: Artificial Sequence
<220> FEATURE:
<223> OTHER INFORMATION: Oligonucleotide

<400> SEQUENCE: 24
gcctcaccag aacctaggca ccaagaccta catctg                            36

<210> SEQ ID NO 25
<211> LENGTH: 40
<212> TYPE: DNA
<213> ORGANISM: Artificial Sequence
<220> FEATURE:
<223> OTHER INFORMATION: Oligonucleotide

<400> SEQUENCE: 25
gcctcaccag aacttaagcg acggaaagac ctacatctgc                        40

<210> SEQ ID NO 26
<211> LENGTH: 7
<212> TYPE: PRT
<213> ORGANISM: Artificial Sequence
<220> FEATURE:
<223> OTHER INFORMATION: Constant region sequence

<400> SEQUENCE: 26

```
Gln Ser Leu Gly Thr Gln Thr
1               5
```

<210> SEQ ID NO 27
<211> LENGTH: 8
<212> TYPE: PRT
<213> ORGANISM: Artificial Sequence
<220> FEATURE:
<223> OTHER INFORMATION: Sequence comprising a salvage receptor binding
      epitope

<400> SEQUENCE: 27

```
Gln Asn Leu Ser Asp Gly Lys Thr
1               5
```

<210> SEQ ID NO 28
<211> LENGTH: 40
<212> TYPE: DNA
<213> ORGANISM: Artificial Sequence
<220> FEATURE:
<223> OTHER INFORMATION: Oligonucleotide

<400> SEQUENCE: 28
gcctcaccag aatattacag atggcaagac ctacatctgc                        40

```
<210> SEQ ID NO 29
<211> LENGTH: 7
<212> TYPE: PRT
<213> ORGANISM: Artificial Sequence
<220> FEATURE:
<223> OTHER INFORMATION: Constant region sequence

<400> SEQUENCE: 29

Gln Ser Leu Gly Thr Gln Thr
1               5

<210> SEQ ID NO 30
<211> LENGTH: 8
<212> TYPE: PRT
<213> ORGANISM: Artificial Sequence
<220> FEATURE:
<223> OTHER INFORMATION: Sequence comprising a salvage receptor binding
      epitope

<400> SEQUENCE: 30

Gln Asn Ile Ser Asp Gly Lys Thr
1               5

<210> SEQ ID NO 31
<211> LENGTH: 8
<212> TYPE: PRT
<213> ORGANISM: Artificial Sequence
<220> FEATURE:
<223> OTHER INFORMATION: Sequence comprising a salvage receptor binding
      epitope

<400> SEQUENCE: 31

Val Ile Ser Ser His Leu Gly Gln
1               5
```

ALTERED POLYPEPTIDES WITH INCREASED HALF-LIFE

This application is a continuation of application Ser. No. 08/422,112, filed Apr. 14, 1995, now U.S. Pat. No. 6,121,022.

BACKGROUND OF THE INVENTION

1. Field of the Invention

This invention relates to polypeptides that are mutated to contain a salvage receptor binding epitope. More particularly, this invention relates to polypeptides that are cleared through the kidney having an epitope from the Fc region of an IgG molecule, resulting in longer circulatory half-life.

2. Description of Related Literature

It was proposed in 1964 that a specific receptor exists in rapid equilibrium with the intravascular space that protects IgG molecules from degradation. Brambell et al., *Nature*, 203: 1352–1355 (1964). See also Brambell, *The Lancet*, 1087–1093 (1965). The kidney has been shown to be the major site of catabolism of immunoglobulin fragments, according for approximately 90% of their endogenous catabolism. Wochner et al., *J. Exp. Med.*, 126: 207 (1967). The existence of a receptor implies that the Ig molecule has specific sequences, or conformational determinants, that must bind to such a receptor. Since the Fc region of IgG produced by proteolysis has the same in vivo half-life as the intact IgG molecule and Fab fragments are rapidly degraded (Spiegelberg and Wiegle, *J. Exp. Med.*, 121: 323–338 [1965]; Waldmann and Ghetie, "Catabolism of Immunoglobulins," *Progress in Immunol.*, 1: 1187–1191 [Academic Press, New York: 1971]; Spiegelberg, in *Advances in Immunology*, Vol. 19, F. J. Dixon and H. G. Kinkel, eds. [Academic Press, NY: 1974], pp. 259–294; and reviewed by Zuckier et al., *Semin. Nucl. Med.*, 19: 166–186 [1989]), it was believed that the relevant sequences of mouse $IgG_{2b}$ were in the CH2 or CH3 domain and that deletion of one or the other domain would give rise to rapid degradation. In fact, the CH2 domain fragment of human IgG produced by trypsin digestion of the Fc fragment persisted in the circulation of rabbits for as long as the Fc fragment or IgG molecule; in contrast, the CH3 domain (pFc') fragment of human IgG also produced by trypsin digestion of the Fc fragment was rapidly eliminated, indicating that the catabolic site of IgG is located in the CH2 domain. Ellerson et al., *J. Immunol.*, 116: 510 (1976); Yasmeen et al., *J. Immunol.*, 116: 518 (1976). Other studies have shown that sequences in the CH3 domain are important in determining the different intravascular half-lives of $IgG_{2b}T$ and $IgG_{2a}h$ antibodies in the mouse. Pollock et al., *Eur. J. Immunol.*, 20: 2021–2027 (1990).

The catabolic rates of IgG variants that do not bind the high-affinity Fc receptor FcRI or C1q are indistinguishable from the rate of clearance of the parent wild-type antibody, indicating that the catabolic site is distinct from the sites involved in FcRI or C1q binding. Wawrzynczak et al., *Molec. Immunol.*, 29: 221 (1992). Also, removal of carbohydrate residues from the IgG molecule or Fc fragment has either a minor role in or no effect on the in vivo half-life, and the extent of this effect depends on the isotype of the IgG molecule. Nose and Wigzell, *Proc. Natl. Acad. Sci. USA*, 80: 6632 (1983); Tao and Morrison, *J. Immunol.*, 143: 2595 (1989); Wawrzynczak et al., *Mol. Immunol.*, 29: 213 (1992).

*Staphylococcal* protein A-IgG complexes were found to clear more rapidly from the serum than uncomplexed IgG molecules. Dima et al., *Eur. J. Immunol.*, 13: 605 (1983). To determine if residues near the Fc-SpA interface are involved in IgG clearance, Kim et al., *Eur. J. Immunol.*, 24: 542–548 (1994) performed site-directed mutagenesis to change amino acid residues of a recombinant Fc-hinge fragment derived from the murine immunoglobulin G1 molecule and determine the effects of these mutations on the pharmacokinetics of the Fc-hinge fragment. The authors showed that the site of the IgG1 molecule that controls the catabolic rate (the "catabolic site") is located at the CH2—CH3 domain interface and overlaps with the *Staphylococcal* protein A binding site. See also WO 93/22332 published Nov. 11, 1993. The concentration catabolism phenomenon is also studied in Zuckier et al., *Cancer*, 73: 794–799 (1994). IgG catabolism is also discussed by Masson, *J. Autoimmunity*, 6: 683–689 (1993).

WO 94/04689 discloses a protein with a cytotoxic domain, a ligand-binding domain and a peptide linking these two domains comprising an IgG constant region domain having the property of increasing the half-life of the protein in mammalian serum.

A stereo drawing of a human Fc fragment and its complex with fragment B of Protein A from *Staphylococcus aureus* is provided by Deisenhofer, *Biochemistry*, 20: 2364 (1981).

It has been shown that clearance is greatly reduced when the effective molecular size exceeds 70 kDa, the glomerular filtration cutoff size. Knauf et al., "Relationship of Effective Molecular Size to Systemic Clearance in Rats of Recombinant Interleukin-2 Chemically Modified with Water-soluble Polymers," *J. Biochem.*, 263: 15064–15070 (1988).

SUMMARY OF THE INVENTION

Accordingly, in one embodiment the invention provides a polypeptide variant of a polypeptide of interest which polypeptide of interest is cleared from the kidney and does not contain a Fc region of an IgG, which variant comprises a salvage receptor binding epitope of an Fc region of an IgG, and which variant has a longer in vivo half-life than the polypeptide of interest.

In another aspect, the invention provides nucleic acid encoding the polypeptide variant, a replicable vector comprising the nucleic acid, a host cell comprising the nucleic acid, and a method for producing a polypeptide variant comprising culturing the host cells in culture medium and recovering the polypeptide variant from the host cell culture. The nucleic acid molecule may be labeled or unlabeled with a detectable moiety.

In a further aspect, the invention supplies a polypeptide that is not an Fc, which polypeptide comprises one or more of the sequences (5' to 3'): HQNLSDGK (SEQ ID NO: 1), HQNISDGK (SEQ ID NO: 2), or VISSHLGQ (SEQ ID NO: 31), and which polypeptide also comprises the sequence: PKNSSMISNTP (SEQ ID NO: 3).

In a still further aspect, the invention provides a method for preparing a polypeptide variant comprising altering a polypeptide of interest that is cleared from the kidney and does not contain an Fc region of an IgG so that it comprises a salvage receptor binding epitope of an Fc region of an IgG and has an increased in vivo half-life.

In a still additional embodiment, the invention supplies a method for preparing a polypeptide variant having an increased in vivo half-life comprising:

(1) identifying the sequence and conformation of a salvage receptor binding epitope on an Fc region of an IgG molecule;

(2) altering the sequence of a polypeptide of interest that is cleared from the kidney and does not contain an Fc region to include the sequence and conformation of the identified binding epitope;

(3) testing the altered polypeptide of step (2) for longer in vivo half-life than that of the polypeptide of interest; and (4) if the polypeptide does not have a longer in vivo half-life, further altering the sequence of the polypeptide of interest to include the sequence and conformation of the identified binding epitope and testing for longer in vivo half-life until longer in vivo half-life is obtained.

In a still further aspect, the invention provides a method for treating an LFA-1-mediated disorder comprising administering to a mammal, preferably a patient, in need of such treatment an effective amount of the variant set forth above wherein the polypeptide is a Fab, a (Fab')$_2$, a diabody, a Fv fragment, a single-chain Fv fragment, or a receptor and acts as an LFA-1 antagonist. More preferably, this variant is a Fab or (Fab')$_2$ of anti-LFA-1 [such as an anti-CD18 Fab or (Fab')$_2$], with increased serum half-life as set forth herein.

In another embodiment, the invention provides a method for detecting CD11a or CD18 in vitro or in vivo comprising contacting the anti-CD11a or CD18 antibody fragment variant herein with a sample, especially a serum sample, suspected of containing the CD11a or CD18 and detecting if binding has occurred.

The Fc region is to be located (transplanted) to a region of the polypeptide of interest that will not alter its conformation so that it loses biological activity and is to be located so that it will not interfere with the polypeptide's ability to bind with a ligand or antigen to maintain biological activity.

BRIEF DESCRIPTION OF THE DRAWINGS

In FIG. 1A, the Fab v1B variant is designated by solid squares, the Fab control is indicated by solid diamonds, the Fab v2 variant is indicated by solid triangles, the Fab v1 variant is indicated by solid circles, and the double-disulfide F(ab')$_2$ is indicated by open circles. In FIG. 1B, the Fab control is designated as solid triangles, the variant Fab v2 is designated by open circles; the variant Fab v1 is designated by open squares; the variant Fab v1B is designated by solid circles; and the double-disulfide F(ab')$_2$ is designated by solid squares. The molecules are more fully described in the tables herein.

FIGS. 2A and 2B depict an alignment of the relevant portions of the consensus amino acid sequences of the human IgG1 CH1 domain (SEQ ID NO:4), the human IgG2 CH1 domain (SEQ ID NO: 5), the human IgG3 CH1 domain (SEQ ID NO: 6), the human IgG4 CH1 domain (SEQ ID NO: 7), the human kappa CL domain (SEQ ID NO: 8), and the human lamda CL domain (SEQ ID NO:9), in alignment with the Fab v1b variant derived from anti-CD18 antibody (SEQ ID NO:10), which is described in Example 1. In these figures, amino acid residues and/or positions of interest of most importance to the invention within the sequence of Fab v1b (i.e., SEQ ID NOS:3 and 1) are designated by underlining and asterisks, respectively.

DETAILED DESCRIPTION OF THE PREFERRED EMBODIMENTS

Definitions

Figure 1A:
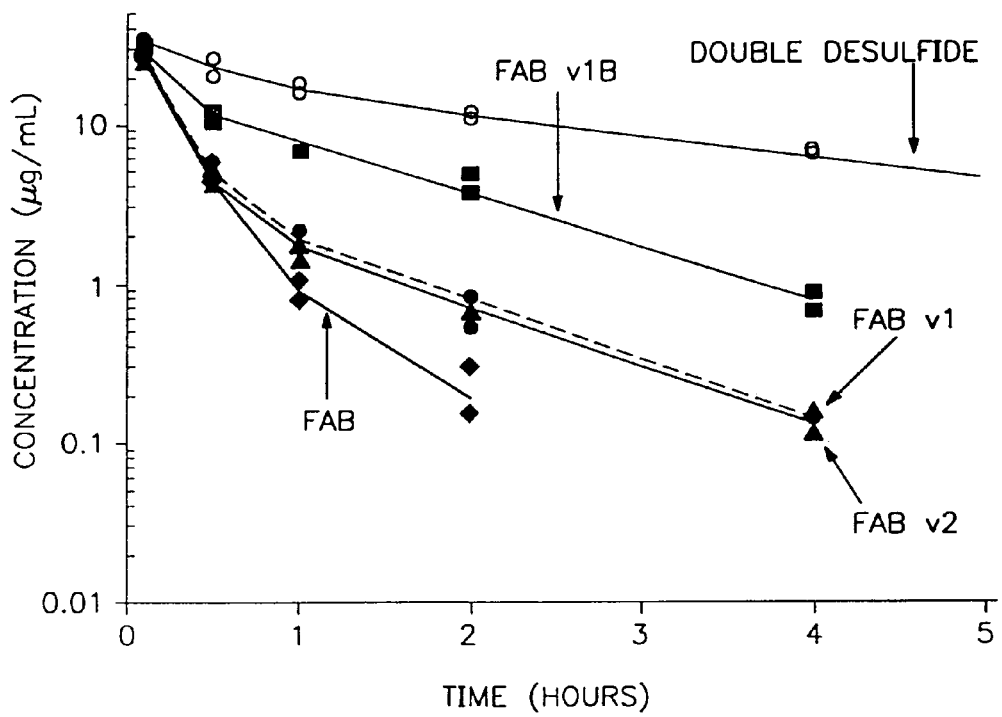
FIGS. 1A and 1B depict the serum pharmacokinetics of five Fab or (Fab')$_2$ constructs in mice after single intravenous doses of 2 mg/kg.

As used herein, "polypeptide of interest" refers to a polypeptide that has a biological activity, is cleared from the kidney, and does not contain a Fc region of an IgG. An "Fc region of an IgG" refers to the Fc portion of an immunoglobulin of the isotype IgG, as is well known to those skilled in the art of antibody technology. Examples of such polypeptides are peptides and proteins, whether from eukaryotic sources such as, e.g., yeast, avians, plants, insects, or mammals, or from bacterial sources such as, e.g., *E. coli*. The polypeptide of interest may be isolated from natural sources or made synthetically or recombinantly. In a preferred embodiment, the polypeptide of interest contains an Ig domain or Ig-like domain, e.g., an antigen-binding domain.

Clearance of polypeptides of interest from the kidney depends at least in part on the molecular weight of the polypeptide. Polypeptides of too large a molecular weight will not clear the kidneys of a mammal. One example of a test to determine whether the polypeptide of interest (or variant) clears the kidney is a clinical study wherein the polypeptide of interest or variant is labeled with a detectable marker and administered to the same type of mammal that will be treated, using a treatment regimen the same as would be used in the actual treatment. Thereafter, a clinical sample of the urine of the mammal is taken and analyzed to determine if the label is detected therein. If the label is detected, the polypeptide of interest or variant has cleared the kidneys.

As a general rule, polypeptides clearing the kidney have a molecular weight in the range of about 5,000–10,000 daltons, although molecules with somewhat higher or lower molecular weights may also meet the criteria of this invention if they can pass the renal clearance test noted above.

The polypeptide of interest is biologically active if it has an in vivo effector or antigenic function or activity that is directly or indirectly caused or performed by the polypeptide (whether in its native or denatured conformation) or a fragment thereof. Effector functions include receptor binding and any carrier binding activity, agonism or antagonism of the polypeptide of interest, especially transduction of a proliferative signal including replication, DNA regulatory function, modulation of the biological activity of various growth factors, receptor activation, deactivation, up- or down-regulation, cell growth or differentiation, and the like. Biological activity includes possession of an epitope or antigenic site that is capable of cross-reacting with antibodies raised against the polypeptide of interest or mammalian equivalents thereof.

Examples of mammalian polypeptides of interest include molecules such as, e.g., renin, a growth hormone, including human growth hormone; bovine growth hormone; growth hormone releasing factor; parathyroid hormone; thyroid stimulating hormone; lipoproteins; α1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance;

relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-β; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1–3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; an anti-HER-2 antibody without a native Fc region of an IgG; superoxide dismutase; T-cell receptors; surface membrane proteins; decay accelerating factor; viral antigen such as, for example, a portion of the AIDS envelope; transport proteins; homing receptors; addressins; regulatory proteins; antibodies without a native Fc region of an IgG; and fragments of any of the above-listed polypeptides.

The preferred polypeptides of interest are mammalian polypeptides. Examples of such mammalian polypeptides include antibody fragments such as Fv, Fab, (Fab')$_2$, and an anti-HER-2 fragment without the IgGFc domain, t-PA, gp120, DNase, IGF-I, IGF-II, brain IGF-I, growth hormone, relaxin chains, growth hormone releasing factor, insulin chains or pro-insulin, urokinase, immunotoxins, neurotrophins, and antigens. More preferably, the polypeptide is a Fab, a (Fab')$_2$, a diabody, a Fv fragment, a single-chain Fv fragment, or a receptor. Even more preferably, the polypeptide is an anti-IgE, anti-HER2, or anti-CD18 Fab or (Fab')$_2$, and most preferably is human or humanized.

As used herein, "polypeptide variant" refers to an amino acid sequence variant of the polypeptide of interest, including variants with one or more amino acid substitutions, insertions, and/or deletions. Such variants are biologically active as defined above and necessarily have less than 100% sequence identity with the polypeptide of interest. In a preferred embodiment, the biologically active polypeptide variant has an amino acid sequence sharing at least about 70% amino acid sequence identity with the polypeptide of interest, preferably at least about 75%, more preferably at least about 80%, still more preferably at least about 85%, even more preferably at least about 90%, and most preferably at least about 95%.

"In vivo half life" means the half-life of the polypeptide of interest or polypeptide variant circulating in the blood of a given mammal.

As used herein, the term "salvage receptor binding epitope" refers to an epitope of the Fc region of an IgG molecule (e.g., IgG1, IgG2, IgG3, and IgG4) that is responsible for increasing the in vivo serum half-life of the IgG molecule. As an example, FIGS. 2A and 2B show representative epitopes in underlining and the important residues in asterisks. The IgG1, IgG2, and IgG4 isotypes are preferred for determining the salvage receptor binding eptiope.

"Polymerase chain reaction" or "PCR" refers to a procedure or technique in which minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51: 263 (1987); Erlich, ed., *PCR Technology*, (Stockton Press, NY, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains (Clothia et al., *J. Mol. Biol.*, 186: 651–663 [1985]; Novotny and Haber, *Proc. Natl. Acad. Sci. USA*, 82: 4592–4596 [1985]).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., supra). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and binding site. This region consists of a dimer of one heavy- and one light-chain variable domain in tight, non-covalent association. It is in this configuration that the three CDRs of each variable domain interact to define an antigen-binding site on the surface of the $V_H$—$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun, A. in *The Pharmacology of Monoclonal Antibodies*, vol. 113, Rosenburg and Moore eds., Springer-Verlag, New York, pp. 269–315 (1994).

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The term "antibody" is used in the broadest sense and specifically covers single monoclonal antibodies (including agonist and antagonist antibodies), antibody compositions with polyepitopic specificity, bispecific antibodies, diabodies, and single-chain molecules, as well as antibody fragments (e.g., Fab, F(ab')$_2$, and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature*, 256: 495 (1975), or may be made by recombinant DNA methods (see, e.g., U.S. Pat. No. 4,816,567 [Cabilly et al.]). The "monoclonal antibodies" may also be isolated from phage antibody libraries using the techniques described in Clackson et al., *Nature*, 352: 624–628 (1991) and Marks et al., *J. Mol. Biol.*, 222: 581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., *Proc. Natl. Acad. Sci. USA*, 81: 6851–6855 [1984]).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details see: Jones et al., *Nature*, 321: 522–525 (1986); Reichmann et al., *Nature*, 332: 323–329 (1988); and Presta, *Curr. Op. Struct. Biol.*, 2: 593–596 (1992). The humanized antibody includes a Primatized™ antibody wherein the antigen-binding region of the antibody is derived from an antibody produced by immunizing macaque monkeys with the antigen of interest.

"Non-immunogenic in a human" means that upon contacting the polypeptide of interest or polypeptide variant in a pharmaceutically acceptable carrier and in a therapeutically effective amount with the appropriate tissue of a human, no state of sensitivity or resistance to the polypeptide of interest or variant is demonstrable upon the second administration of the polypeptide of interest or variant after an appropriate latent period (e.g., 8 to 14 days).

The term "diabodies" refers to small antibody fragments with two antigen-binding sites, which fragments comprise a heavy-chain variable domain ($V_H$) connected to a light-chain variable domain ($V_L$) on the same polypeptide chain ($V_H$ —$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Holliger et al., *Proc. Natl. Acad. Sci. USA*, 90: 6444–6448 (1993).

The term "LFA-1-mediated disorders" refers to pathological states caused by cell adherence interactions involving the LFA-1 receptor on lymphocytes. Examples of such disorders include T cell inflammatory responses such as inflammatory skin diseases including psoriasis; responses associated with inflammatory bowel disease (such as Crohn's disease and ulcerative colitis); adult respiratory distress syndrome; dermatitis; meningitis; encephalitis; uveitic; allergic conditions such as eczema and asthma and other conditions involving infiltration of T cells and chronic inflammatory responses; skin hypersensitivity reactions (including poison ivy and poison oak); atherosclerosis; leukocyte adhesion deficiency; autoimmune diseases such as rheumatoid arthritis, systemic lupus erythematosus (SLE), diabetes mellitus, multiple sclerosis, Reynaud's syndrome, autoimmune thyroiditis, experimental autoimmune encephalomyelitis, Sjorgen's syndrome, juvenile onset diabetes, and immune responses associated with delayed hypersensitivity mediated by cytokines and T-lymphocytes typically found in tuberculosis, sarcoidosis, polymyositis, granulomatosis and vasculitis; pernicious anemia; diseases involving leukocyte diapedesis; CNS inflammatory disorder, multiple organ injury syndrome secondary to septicaemia or trauma; autoimmune haemolytic anemia; myethemia gravis; antigen-antibody complex mediated diseases; all types of transplantations, including graft vs. host or host vs. graft disease; hemorrhagic shock; pulmonary oxygen toxicity; pulmonary fibrosis; wound repair; B-cell lymphomas; etc.

In particular, the preferred indications for antibodies to CD11a or CD11b are psoriasis, transplant rejection, asthma, wound repair, and pulmonary fibrosis; the preferred indications for antibodies to CD18 are hemorrhagic shock, meningitis; encephalitis; multiple sclerosis; asthma; and pulmonary oxygen toxicity; and the preferred indication for antibodies to CD20 is B-cell lymphoma.

"Treatment" refers to both therapeutic treatment and prophylactic or preventative measures. Those in need of treatment include those already with the disorder as well as those prone to have the disorder or those in which the disorder is to be prevented.

"Mammal" for purposes of treatment refers to any animal classified as a mammal, including humans, domestic and farm animals, and zoo, sports, or pet animals, such as dogs, horses, cats, sheep, pigs, cows, etc. Preferably, the mammal herein is human.

The term "LFA-1 antagonist" generally refers to an antibody directed against either CD11a or CD18 or both, but also includes soluble forms of ICAM-1 (e.g., the ICAM-1 extracellular domain), antibodies to ICAM-1, and fragments thereof, or other molecules capable of inhibiting the interaction of LFA-1 and ICAM-1.

The term "anti-LFA-1 antibody" or "anti-LFA-1 MAb" refers to an antibody directed against either CD11a or CD18 or both. The anti-CD11a antibodies include, e.g., MHM24 (Hildreth et al., *Eur. J. Immunol.*, 13: 202–208 [1983]), R3.1 (IgG1; Rothlein, Boehringer Ingelheim Pharmaceuticals, Inc., Ridgefield, Conn.), 25-3 (or 25.3; an IgG1 available from Immunotech, France; see Olive et al., in Feldmann, ed., *Human T cell Clones, A new Approach to Immune Regulation*, Clifton, N.J., Humana, [1986] p. 173), KBA (IgG2a; Nishimura et al., *Cell. Immunol.*, 107: 32 [1987]; Nishimura et al., *Cell. Immunol.*, 94: 122 [1985]), M7/15 (IgG2b; Springer et al., Immunol. Rev., 68: 171 [1982]), IOT16 (Vermot Desroches et al., *Scand. J. Immunol.*, 33: 277–286 [1991]), SPV$_L$ 7 (Vermot Desroches et al., supra), and M17 (IgG2a; available from ATCC, which are rat anti-murine CD11a antibodies).

Examples of anti-CD18 antibodies include MHM23 (Hildreth et al, supra), M18/2 (IgG2a; Sanches-Madrid et al., *J. Exp. Med.*, 158: 586 [1983]), H52 (Fekete et al., *J. Clin. Lab Immunol.*, 31: 145–149 [1990]), Mas191c (Vermot Desroches et al., supra), IOT18 (Vermot Desroches et al., supra), 60.3 (Taylor et al., *Clin. Exp. Immunol.*, 71: 324–328 [1988]), and 60.1 (Campana et al., *Eur. J. Immunol.*, 16: 537–542 [1986]).

Other examples of suitable LFA-1 antagonists, including antibodies, are described in Hutchings et al., *Nature*, 348: 639 (1990), WO 91/18011 published Nov. 28, 1991, WO 91/16928 published Nov. 14, 1991, WO 91/16927 published Nov. 14, 1991, Can. Pat. Appln. 2,008,368 published Jun. 13, 1991, WO 90/15076 published Dec. 13, 1990, WO 90/10652 published Sep. 20, 1990, EP 387,668 published Sep. 19, 1990, EP 379,904 published Aug. 1, 1990, EP 346,078 published Dec. 13, 1989, U.S. Pat. No. 5,071,964, U.S. Pat. No. 5,002,869, Australian Pat. Appln. 8815518 published Nov. 10, 1988, EP 289,949 published Nov. 9, 1988, and EP 303,692 published Feb. 22, 1989.

Modes for Carrying Out the Invention

1. General Description of the Invention

The current invention is concerned with incorporating a salvage receptor binding epitope of the Fc region of an IgG into a polypeptide of interest so as to increase its circulatory half-life, but so as not to lose its biological activity. This can take place by any means, such as by mutation of the appropriate region in the polypeptide of interest to mimic the Fc region or by incorporating the epitope into a peptide tag that is then fused to the polypeptide of interest at either end or in the middle or by DNA or peptide synthesis.

A systematic method for preparing such a polypeptide variant having an increased in vivo half-life comprises several steps. The first involves identifying the sequence and conformation of a salvage receptor binding epitope on an Fc region of an IgG molecule. Once this epitope is identified, the sequence of the polypeptide of interest is modified to include the sequence and conformation of the identified binding epitope. After the sequence is mutated, the polypeptide variant is tested to see if it has a longer in vivo half-life than that of the original polypeptide, ie., the polypeptide of interest. If the polypeptide variant does not have a longer in vivo half-life upon testing, its sequence is further altered to include the sequence and conformation of the identified binding epitope. The altered polypeptide is tested for longer in vivo half-life, and this process is continued until a molecule is obtained that exhibits a longer in vivo half-life.

The salvage receptor binding epitope being thus incorporated into the polypeptide of interest is any suitable such epitope as defined above, and its nature will depend, e.g., on the type of polypeptide being modified. The transfer is made such that the biological activity of the polypeptide of interest is maintained, i.e., the transferred portion does not adversely affect the conformation of the polypeptide of interest or affect its binding to ligands that confers its biological activity. For example, if the polypeptide of interest is an antibody, the salvage receptor binding epitope is not placed so as to interfere with an antigen-binding site of the antibody.

Preferably, the polypeptide of interest contains an Ig domain or Ig-like domain and the salvage receptor binding epitope is placed so that it is located within this Ig domain or Ig-like domain. More preferably, the epitope constitutes a region wherein any one or more amino acid residues from one or two loops of the Fc domain are transferred to an analogous position of the Ig domain or Ig-like domain of the polypeptide of interest. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of an Ig or to a Ig-like domain. Alternatively, the epitope is taken from the CH2 domain of the Fc region and transferred to the CL region or $V_L$ region, or both, of an Ig or to an Ig-like domain of the polypeptide of interest.

For example, for purposes of discussing variants wherein the polypeptide of interest is anti-CD18, reference is made to FIG. 2, which illustrates the relevant consensus primary structures of various Igs, i.e., human IgG1 CH1 domain, human IgG2 CH1 domain, human IgG3 CH1 domain, human IgG4 CH1 domain, human kappa CL domain, and human lambda CL domain, as well as the specific sequence for Fab v1b, a preferred anti-CD18 Fab variant herein. Further, FIG. 2 indicates the residues of Fab v1b that are of interest and of most importance. In a preferred embodiment, the residues of importance are those with an asterisk in FIG. 2, i.e., in one loop of Fab v1b, MIS with a T residue one amino acid C-terminal to MIS, and in another loop of Fab v1b, HQN with a D residue two amino acids C-terminal to HQN and a K residue one amino acid C-terminal to the D residue.

In one most preferred embodiment, the salvage receptor binding epitope comprises the sequence (5' to 3'):

PKNSSMISNTP (SEQ ID NO: 3), and optionally further comprises a sequence selected from the group consisting of HQSLGTQ (SEQ ID NO: 11), HQNLSDGK (SEQ ID NO: 1), HQNISDGK (SEQ ID NO: 2), or VISSHLGQ (SEQ ID NO: 31), particularly where the polypeptide of interest is a Fab or (Fab')$_2$.

In another most preferred embodiment, the salvage receptor binding epitope is a polypeptide that is not an Fc containing the sequence(s)(5' to 3'): HQNLSDGK (SEQ ID NO: 1), HQNISDGK (SEQ ID NO: 2), or VISSHLGQ (SEQ ID NO: 31) and the sequence: PKNSSMISNTP (SEQ ID NO: 3). This epitope is suitably fused to the polypeptide of interest, and in a preferred aspect is contained on a peptide that is fused to the polypeptide of interest. Examples of polypeptides of interest suitable for this purpose include those which will have altered secondary or tertiary structure, with adverse consequences, if the sequence thereof is mutated, such as growth hormone or nerve growth factor.

In one embodiment, the variants can be prepared by recombinant means. Thus, nucleic acid encoding the variant is prepared, placed into a replicable vector and the vector is used to transfect or transform suitable host cells for expression. The polypeptide variant is produced by culturing the host cells in a culture medium and recovering the polypeptide variant from the host cell culture. If the polypeptide variant is being secreted, it is recovered from the culture medium. In another embodiment, the polypeptide variant is prepared by altering a polypeptide of interest that is cleared from the kidney and does not contain an Fc region of an IgG so that it comprises a salvage receptor binding epitope of an Fc region of an IgG and has an increased in vivo half-life. The altering step is preferably conducted by Kunkel, site-directed, cassette, or PCR mutagenesis. Kunkel mutagenesis is described, e.g., by Kunkel, *Proc. Natl. Acad. Sci. U.S.A.,* 82: 488–492 (1985).

2. Preparation of Polypeptides of Interest and Their Variants

Most of the discussion below pertains to production of the polypeptide of interest or polypeptide variant by culturing cells transformed with a vector containing the nucleic acid encoding the polypeptide of interest or polypeptide variant and recovering the polypeptide of interest or variant from the cell culture. It is further envisioned that the polypeptide of interest may be produced by homologous recombination, as provided for in WO 91/06667 published 16 May 1991. Briefly, this method involves transforming primary mammalian cells containing endogenous polypeptide (e.g., human cells if the desired polypeptide is human) with a construct (i.e., vector) comprising an amplifiable gene (such as dihydrofolate reductase [DHFR] or others discussed below) and at least one flanking region of a length of at least about 150 bp that is homologous with a DNA sequence at the locus of the coding region of the gene of the polypeptide of interest to provide amplification of the gene encoding the polypeptide of interest. The amplifiable gene must be at a site that does not interfere with expression of the gene encoding the polypeptide of interest. The transformation is conducted such that the construct becomes homologously integrated into the genome of the primary cells to define an amplifiable region.

Primary cells comprising the construct are then selected for by means of the amplifiable gene or other marker present in the construct. The presence of the marker gene establishes the presence and integration of the construct into the host genome. No further selection of the primary cells need be made, since selection will be made in the second host. If desired, the occurrence of the homologous recombination event can be determined by employing PCR and either sequencing the resulting amplified DNA sequences or determining the appropriate length of the PCR fragment when DNA from correct homologous integrants is present and expanding only those cells containing such fragments. Also if desired, the selected cells may be amplified at this point by stressing the cells with the appropriate amplifying agent (such as methotrexate if the amplifiable gene is DHFR), so that multiple copies of the target gene are obtained. Preferably, however, the amplification step is not conducted until after the second transformation described below.

After the selection step, DNA portions of the genome, sufficiently large to include the entire amplifiable region, are isolated from the selected primary cells. Secondary mammalian expression host cells are then transformed with these genomic DNA portions and cloned, and clones are selected that contain the amplifiable region. The amplifiable region is then amplified by means of an amplifying agent if not already amplified in the primary cells. Finally, the secondary expression host cells now comprising multiple copies of the amplifiable region containing the polypeptide of interest are grown so as to express the gene and produce the polypeptide.

A. Isolation of DNA Encoding Polypeptide of Interest

The DNA encoding the polypeptide of interest may be obtained from any cDNA library prepared from tissue believed to possess the mRNA encoding the polypeptide of interest and to express it at a detectable level. The gene encoding the polypeptide of interest may also be obtained from a genomic library or by in vitro oligonucleotide synthesis, assuming the complete nucleotide or amino acid sequence is known.

Libraries are screened with probes designed to identify the gene of interest or the protein encoded by it. For cDNA expression libraries, suitable probes include monoclonal or polyclonal antibodies that recognize and specifically bind to the polypeptide of interest; oligonucleotides of about 20–80 bases in length that encode known or suspected portions of the cDNA encoding the polypeptide of interest from the same or different species; and/or complementary or homologous cDNAs or fragments thereof that encode the same or a similar gene. Appropriate probes for screening genomic DNA libraries include, but are not limited to, oligonucleotides, cDNAs, or fragments thereof that encode the same or a similar gene, and/or homologous genomic DNAs or fragments thereof. Screening the cDNA or genomic library with the selected probe may be conducted using standard procedures as described in Chapters 10–12 of Sambrook et al., *Molecular Cloning: A Laboratory Manual* (New York: Cold Spring Harbor Laboratory Press, 1989).

An alternative means to isolate the gene encoding the polypeptide of interest is to use PCR methodology as described in Section 14 of Sambrook et al., supra. This method requires the use of oligonucleotide probes that will hybridize to the polypeptide of interest. Strategies for selection of oligonucleotides are described below.

A preferred method of practicing this invention is to use carefully selected oligonucleotide sequences to screen cDNA libraries from various tissues.

The oligonucleotide sequences selected as probes should be of sufficient length and sufficiently unambiguous that false positives are minimized. The actual nucleotide sequence(s) is usually based on conserved or highly homologous nucleotide sequences. The oligonucleotides may be degenerate at one or more positions. The use of degenerate oligonucleotides may be of particular importance where a library is screened from a species in which preferential codon usage is not known. The oligonucleotide must be labeled such that it can be detected upon hybridization to DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

Of particular interest is the nucleic acid encoding the polypeptide of interest that encodes a full-length polypeptide. In some preferred embodiments, the nucleic acid sequence includes the polypeptide of interest's signal sequence. Nucleic acid having all the protein coding sequence is obtained by screening selected cDNA or genomic libraries using the deduced amino acid sequence disclosed herein for the first time, and, if necessary, using conventional primer extension procedures as described in Section 7.79 of Sambrook et al., supra, to detect precursors and processing intermediates of mRNA that may not have been reverse-transcribed into cDNA.

B. Preparation of Variants of Polypeptide of Interest

The variants of the polypeptide of interest are suitably prepared by introducing appropriate nucleotide changes as set forth above for the Fc region into the DNA encoding the polypeptide of interest, or by in vitro synthesis of the desired polypeptide variant. Such variants include, for example, deletions from, or insertions or substitutions of, residues within the amino acid sequence of the polypeptide of interest so that it contains the proper epitope and has a longer half-life in serum. Any combination of deletion, insertion, and substitution is made to arrive at the final construct, provided that the final construct possesses the desired characteristics. The amino acid changes also may alter post-translational processes of the polypeptide of interest, such as changing the number or position of glycosylation sites. Moreover, like most mammalian genes, the polypeptide of interest might be encoded by multi-exon genes.

For the design of amino acid sequence variants of the polypeptide of interest, the location of the mutation site and the nature of the mutation will be determined by the specific polypeptide of interest being modified. For example, an immunoglobulin or immunoglobulin-like domain will be initially modified by locating loops that are structurally similar to the two loops in IgG CH2 that contain the salvage receptor epitope. The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1–3.

A useful method for identification of certain residues or regions of the polypeptide of interest that are preferred locations for mutagenesis is called "alanine scanning mutagenesis," as described by Cunningham and Wells, *Science*, 244: 1081–1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis is conducted at the target codon or region and the variants produced are screened for increased circulatory half-life.

Amino acid sequence deletions generally range from about 1 to 30 residues, more preferably about 1 to 10 residues, and typically are contiguous. Contiguous deletions ordinarily are made in even numbers of residues, but single or odd numbers of deletions are within the scope hereof. As an example, deletions may be introduced into regions of low homology among LFA-1 antibodies which share the most sequence identity to the amino acid sequence of the polypeptide of interest to modify the half-life of the polypeptide. Deletions from the polypeptide of interest in areas of substantial homology with one of the binding sites of other ligands will be more likely to modify the biological activity of the polypeptide of interest more significantly. The number of consecutive deletions will be selected so as to preserve the tertiary structure of the polypeptide of interest in the affected domain, e.g., beta-pleated sheet or alpha helix.

Amino acid sequence insertions include amino- and/or carboxyl-terminal fusions ranging in length from one residue to polypeptides containing a hundred or more residues, as well as intra-sequence insertions of single or multiple amino acid residues. Intra-sequence insertions (i.e., insertions within the mature polypeptide sequence) may range generally from about 1 to 10 residues, more preferably 1 to 5, most preferably 1 to 3. Insertions are preferably made in even numbers of residues, but this is not required. Examples of insertions include insertions to the internal portion of the polypeptide of interest, as well as N- or C-terminal fusions with proteins or peptides containing the desired epitope that will result, upon fusion, in an increased half-life.

A third group of variants are amino acid substitution variants. These variants have at least one amino acid residue in the polypeptide molecule removed and a different residue inserted in its place. The sites of greatest interest for substitutional mutagenesis include one or two loops in antibodies. Other sites of interest are those in which particular residues of the polypeptide obtained from various species are identical among all animal species of the polypeptide of interest, this degree of conservation suggesting importance in achieving biological activity common to these molecules. These sites, especially those falling within a sequence of at least three other identically conserved sites, are substituted in a relatively conservative manner. Such conservative substitutions are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function of the polypeptide of interest are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

It may be desirable to inactivate one or more protease cleavage sites that are present in the molecule. These sites are identified by inspection of the encoded amino acid sequence, in the case of trypsin, e.g., for an arginyl or lysinyl residue. When protease cleavage sites are identified, they are rendered inactive to proteolytic cleavage by substituting the targeted residue with another residue, preferably a basic residue such as glutamine or a hydrophilic residue such as serine; by deleting the residue; or by inserting a prolyl residue immediately after the residue.

In another embodiment, any methionyl residues other than the starting methionyl residue of the signal sequence, or any residue located within about three residues N- or C-terminal to each such methionyl residue, is substituted by another residue (preferably in accord with Table 1) or deleted. Alternatively, about 1–3 residues are inserted adjacent to such sites.

Any cysteine residues not involved in maintaining the proper conformation of the polypeptide of interest also may be substituted, generally with serine, to improve the oxidative stability of the molecule and prevent aberrant crosslinking.

In the first embodiment, nucleic acid molecules encoding amino acid sequence variants of the polypeptide of interest are prepared by a variety of methods known in the art. These methods include, but are not limited to, preparation by oligonucleotide-mediated (or site-directed) mutagenesis, PCR mutagenesis, and cassette mutagenesis of an earlier prepared variant or a non-variant version of the polypeptide on which the variant herein is based ("polypeptide of interest").

Oligonucleotide-mediated mutagenesis is a preferred method for preparing substitution, deletion, and insertion polypeptide variants herein. This technique is well known in the art as described by Adelman et al., *DNA*, 2: 183 (1983). Briefly, the DNA is altered by hybridizing an oligonucleotide encoding the desired mutation to a DNA template, where the template is the single-stranded form of a plasmid or bacteriophage containing the unaltered or native DNA sequence of the polypeptide to be varied. After hybridization, a DNA polymerase is used to synthesize an entire second complementary strand of the template that will thus incorporate the oligonucleotide primer, and will code for the selected alteration in the DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. USA*, 75: 5765 (1978).

The DNA template can be generated by those vectors that are either derived from bacteriophage M13 vectors (the commercially available M13 mp18 and M13 mp19 vectors are suitable), or those vectors that contain a single-stranded phage origin of replication as described by Viera et al. *Meth. Enzymol.*, 153: 3 (1987). Thus, the DNA that is to be mutated may be inserted into one of these vectors to generate single-stranded template. Production of the single-stranded template is described in Sections 4.21–4.41 of Sambrook et al., supra.

Alternatively, single-stranded DNA template may be generated by denaturing double-stranded plasmid (or other) DNA using standard techniques.

For alteration of the original DNA sequence to generate the polypeptide variants of this invention, the oligonucleotide is hybridized to the single-stranded template under suitable hybridization conditions. A DNA polymerizing enzyme, usually the Klenow fragment of DNA polymerase 1, is then added to synthesize the complementary strand of the template using the oligonucleotide as a primer for synthesis. A heteroduplex molecule is thus formed such that one strand of DNA encodes the mutated form of the polypeptide, and the other strand (the original template) encodes the original, unaltered sequence of the polypeptide. This heteroduplex molecule is then transformed into a suitable host cell, usually a prokaryote such as *E. coli* JM101. After the cells are grown, they are plated onto agarose plates and screened using the oligonucleotide primer radiolabeled with $^{32}$P to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-($\alpha$S) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-($\alpha$S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

DNA encoding polypeptide mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of this invention. While the following discussion refers to DNA, it is understood that the technique also finds application with RNA. The PCR technique generally refers to the following procedure (see Erlich, supra, the chapter by R. Higuchi, p. 61–70): When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 $\mu$g) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp® kits (obtained from Perkin-Elmer Cetus, Norwalk, Conn. and Emeryville, Calif.), and 25 pmole of each oligonucleotide primer, to a final volume of 50 µL. The reaction mixture is overlaid with 35 µL mineral oil. The reaction mixture is denatured for five minutes at 100° C., placed briefly on ice, and then 1 µL *Thermus aquaticus* (Taq) DNA polymerase (5 units/µL, purchased from Perkin-Elmer Cetus) is added below the mineral oil layer. The reaction mixture is then inserted into a DNA Thermal Cycler (purchased from Perkin-Elmer Cetus) programmed as follows:

2 min. 55° C.

30 sec. 72° C., then 19 cycles of the following:

30 sec. 94° C.

30 sec. 55° C., and 30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al., *Gene,* 34: 315 (1985). The starting material is the plasmid (or other vector) comprising the DNA to be mutated. The codon(s) in the DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated DNA sequence.

C. Insertion of Nucleic Acid into Replicable Vector

The nucleic acid (e.g., cDNA or genomic DNA) encoding the polypeptide variant is inserted into a replicable vector for further cloning (amplification of the DNA) or for expression. Many vectors are available, and selection of the appropriate vector will depend on 1) whether it is to be used for DNA amplification or for DNA expression, 2) the size of the nucleic acid to be inserted into the vector, and 3) the host cell to be transformed with the vector. Each vector contains various components depending on its function (amplification of DNA or expression of DNA) and the host cell with which it is compatible. The vector components generally include, but are not limited to, one or more of the following: a signal sequence, an origin of replication, one or more marker genes, an enhancer element, a promoter, and a transcription termination sequence.

(i) Signal Sequence Component

The polypeptide variants of this invention may be produced not only directly, but also as a fusion with a heterologous polypeptide, preferably a signal sequence or other polypeptide having a specific cleavage site at the N-terminus of the mature polypeptide variant. In general, the signal sequence may be a component of the vector, or it may be a part of the DNA that is inserted into the vector. The heterologous signal sequence selected should be one that is recognized and processed (i.e., cleaved by a signal peptidase) by the host cell. For prokaryotic host cells that do not recognize and process the polypeptide of interest's signal sequence, the signal sequence is substituted by a prokaryotic signal sequence selected, for example, from the group consisting of the alkaline phosphatase, penicillinase, Ipp, or heat-stable enterotoxin II leaders. For yeast secretion the original or wild-type signal sequence may be substituted by, e.g., the yeast invertase leader, yeast alpha factor leader (including *Saccharomyces* and *Kluyveromyces* α-factor leaders, the latter described in U.S. Pat. No. 5,010,182 issued 23 Apr. 1991), yeast acid phosphatase leader, mouse salivary amylase leader, carboxypeptidase leader, yeast BAR1 leader, *Humicola lanuginosa* lipase leader, the *C. albicans* glucoamylase leader (EP 362,179 published 4 Apr. 1990), or the signal described in WO 90/13646 published 15 Nov. 1990. In mammalian cell expression the original human signal sequence (i.e., the polypeptide presequence that normally directs secretion of the native polypeptide of interest from which the variant of interest is derived from human cells in vivo) is satisfactory, although other mammalian signal sequences may be suitable, such as signal sequences from other animal polypeptides and signal sequences from secreted polypeptides of the same or related species, as well as viral secretory leaders, for example, the herpes simplex gD signal.

The DNA for such precursor region is ligated in reading frame to DNA encoding the mature polypeptide variant.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 (ATCC 37,017), or from other commercially available bacterial vectors such as, e.g., pKK223-3 (Pharmacia Fine Chemicals, Uppsala, Sweden) and pGEM1 (Promega Biotech, Madison, Wis.), is suitable for most Gram-negative bacteria, the 2 µ plasmid origin is suitable for yeast, and various viral origins (SV40, polyoma, adenovirus, VSV, or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using *Bacillus* species as hosts, for example, by including in the vector a DNA sequence that is complementary to a sequence found in *Bacillus* genomic DNA. Transfection of *Bacillus* with this vector results in homologous recombination with the genome and insertion of the DNA. However, the recovery of genomic DNA encoding the polypeptide variant is more complex than that of an exogenously replicated vector because restriction enzyme digestion is required to excise the DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin (Southern et al., *J. Molec. Appl. Genet.,* 1: 327 [1982]), mycophenolic acid (Mulligan et al., *Science,* 209: 1422 [1980]), or hygromycin (Sugden et al., *Mol. Cell. Biol.,* 5: 410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the polypeptide variant. Amplification is the process by which genes in greater demand for the production of a protein critical for growth are reiterated in tandem within the chromosomes of successive generations of recombinant cells. Increased quantities of the polypeptide variant are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA,* 77: 4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the polypeptide variant. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding the polypeptide variant, wild-type DHFR protein, and another selectable marker such as aminoglycoside 3-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature,* 282: 39 [1979]; Kingsman et al., *Gene,* 7: 141 [1979]; or Tschemper et al., *Gene,* 10: 157 [1980]). The trp1 gene provides a selection marker for a mutant strain of yeast lacking the ability to grow in tryptophan, for example, ATCC No. 44076 or PEP4-1 (Jones, *Genetics,* 85: 12 [1977]). The presence of the trp1 lesion in the yeast host cell genome then provides an effective environment for detecting transformation by growth in the absence of tryptophan. Similarly, Leu2-deficient yeast strains (ATCC No. 20,622 or 38,626) are complemented by known plasmids bearing the Leu2 gene.

In addition, vectors derived from the 1.6 μm circular plasmid pKD1 can be used for transformation of *Kluyveromyces* yeasts. Bianchi et al., *Curr. Genet.,* 12: 185 (1987). More recently, an expression system for large-scale production of recombinant calf chymosin was reported for *K. lactis*. Van den Berg, *Bio/Technology,* 8: 135 (1990). Stable multicopy expression vectors for secretion of mature recombinant human serum albumin by industrial strains of *Kluyveromyces* have also been disclosed. Fleer et al., *Bio/Technology,* 9: 968–975 (1991).

(iv) Promoter Component

Expression and cloning vectors usually contain a promoter that is recognized by the host organism and is operably linked to the nucleic acid. Promoters are untranslated sequences located upstream (5') to the start codon of a structural gene (generally within about 100 to 1000 bp) that control the transcription and translation of particular nucleic acid sequence, such as the nucleic acid sequence of the polypeptide variants herein, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to the DNA encoding the polypeptide variant by removing the promoter from the source DNA by restriction enzyme digestion and inserting the isolated promoter sequence into the vector. The promoter of the polypeptide of interest and many heterologous promoters may be used to direct amplification and/or expression of the DNA. However, heterologous promoters are preferred, as they generally permit greater transcription and higher yields of recombinantly produced polypeptide variant as compared to the promoter of the polypeptide of interest.

Promoters suitable for use with prokaryotic hosts include the β-lactamase and lactose promoter systems (Chang et al., *Nature,* 275: 615 [1978]; and Goeddel et al., Nature, 281: 544 [1979]), alkaline phosphatase, a tryptophan (trp) promoter system (Goeddel, *Nucleic Acids Res.,* 8: 4057 [1980] and EP 36,776) and hybrid promoters such as the tac promoter (deBoer et al., Proc. *Natl. Acad. Sci. USA,* 80: 21–25 [1983]). However, other known bacterial promoters are suitable. Their nucleotide sequences have been published, thereby enabling a skilled worker operably to ligate them to DNA encoding the polypeptide variant (Siebenlist et al., *Cell*, 20: 269 [1980]) using linkers or adaptors to supply any required restriction sites. Promoters for use in bacterial systems also will contain a Shine-Dalgarno (S.D.) sequence operably linked to the DNA encoding the polypeptide variant.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.*, 255: 2073 [1980]) or other glycolytic enzymes (Hess et al., *J. Adv. Enzyme Reg.*, 7: 149 [1968]; and Holland, *Biochemistry*, 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657. Yeast enhancers also are advantageously used with yeast promoters.

Transcription of polypeptide variant from vectors in mammalian host cells is controlled, for example, by promoters obtained from the genomes of viruses such as polyoma virus, fowlpox virus (UK 2,211,504 published, 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the polypeptide variant sequence, provided such promoters are compatible with the host cell systems.

The early and late promoters of the SV40 virus are conveniently obtained as an SV40 restriction fragment that also contains the SV40 viral origin of replication. Fiers et al., *Nature*, 273:113 (1978); Mulligan and Berg, *Science*, 209: 1422–1427 (1980); Pavlakis et al., *Proc. Natl. Acad. Sci. USA*, 78: 7398–7402 (1981). The immediate early promoter of the human cytomegalovirus is conveniently obtained as a HindIII E restriction fragment. Greenaway et al., *Gene*, 18: 355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295: 503–508 (1982) on expressing cDNA encoding immune interferon in monkey cells; Reyes et al., *Nature*, 297: 598–601 (1982) on expression of human β-interferon cDNA in mouse cells under the control of a thymidine kinase promoter from herpes simplex virus; Canaani and Berg, *Proc. Natl. Acad. Sci. USA*, 79: 5166–5170 (1982) on expression of the human interferon β1 gene in cultured mouse and rabbit cells; and Gorman et al., *Proc. Natl. Acad. Sci. USA*, 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding the polypeptide variant of this invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA*, 78: 993 [1981]) and 3' (Lusky et al., *Mol. Cell Bio.*, 3: 1108 [1983]) to the transcription unit, within an intron (Banerji et al., *Cell*, 33: 729 [1983]), as well as within the coding sequence itself (Osborne et al., *Mol. Cell Bio.*, 4: 1293 [1984]). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297: 17–18 (1982) on enhancing elements for activation of eukaryotic promoters. The enhancer may be spliced into the vector at a position 5' or 3' to the polypeptide-variant-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide variant.

(vii) Construction and Analysis of Vectors

Construction of suitable vectors containing one or more of the above-listed components employs standard ligation techniques. Isolated plasmids or DNA fragments are cleaved, tailored, and re-ligated in the form, desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9: 309 (1981) or by the method of Maxam et al., *Methods in Enzymology*, 65: 499 (1980).

(viii) Transient Expression Vectors

Particularly useful in the practice of this invention are expression vectors that provide for the transient expression in mammalian cells of DNA encoding the polypeptide variant. In general, transient expression involves the use of an expression vector that is able to replicate efficiently in a host cell, such that the host cell accumulates many copies of the expression vector and, in turn, synthesizes high levels of a desired polypeptide encoded by the expression vector.

Sambrook et al., supra, pp. 16.17–16.22. Transient expression systems, comprising a suitable expression vector and a host cell, allow for the convenient positive identification of polypeptide variants encoded by cloned DNAs, as well as for the rapid screening of such polypeptides for desired biological or physiological properties. Thus, transient expression systems are particularly useful in the invention for purposes of identifying polypeptide variants that are biologically active.

(ix) Suitable Exemplary Vertebrate Cell Vectors

Other methods, vectors, and host cells suitable for adaptation to the synthesis of the polypeptide variant in recombinant vertebrate cell culture are described in Gething et al., *Nature*, 293: 620–625 (1981); Mantei et al., *Nature*, 281: 40–46 (1979); EP 117,060; and EP 117,058. A particularly useful plasmid for mammalian cell culture production of the polypeptide variant is pRK5 (EP 307,247) or pSVI6B (WO 91/08291 published 13 Jun. 1991). The pRK5 derivative pRK5B (Holmes et al., *Science*, 253: 1278–1280 [1991]) is particularly suitable herein for such expression.

D. Selection and Transformation of Host Cells

Suitable host cells for cloning or expressing the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescens*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X 1776 (ATCC 31,537), *E. coli* DH5α, and *E. coli* W3110 (ATCC 27,325) are suitable. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonAΔ; *E. coli* W3110 strain 9E4, which has the complete genotype tonAΔ ptr3; *E. coli* W3110 strain 27C7 (ATCC 55,244), which has the complete genotype tone ptr3 phoAΔE15 Δ(argF-lac)169 ΔdegP ΔompT kan$^r$; *E. coli* W3110 strain 37D6, which has the complete genotype tonA ptr3 phoAΔE15 Δ(argF-lac) 169 ΔdegP ΔompTΔrbs7 #vG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for polypeptide-variant-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., supra) such as, e.g., *K. lactis* (MW98-8C, CBS683, CBS4574; Louvencourt et al., *J. Bacteriol.*, 737 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra), *K. thermotolerans*, and *K. marxianus; yarrowia* (EP 402, 226); *Pichia pastoris* (EP 183,070; Sreekrishna et al., *J. Basic Microbiol.*, 28: 265–278 [1988]); *Candida; Trichoderma reesia* (EP 244,234); *Neurospora crassa* (Case et al., *Proc. Natl. Acad. Sci. USA*, 76: 5259–5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.*, 112: 284–289 [1983]; Tilburn et al., *Gene*, 26: 205–221 [1983]; Yelton et al., *Proc. Natl. Acad. Sci. USA*, 81: 1470–1474 [1984]) and *A. niger* (Kelly and Hynes, *EMBO J.*, 4: 475–479 [1985]).

Suitable host cells for the production of the polypeptide variant are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology*, 6: 47–55 (1988); Miller et al., in *Genetic Engineering*, Setlow, J. K. et al., eds., Vol. 8 (Plenum Publishing, 1986), pp. 277–279; and Maeda et al., *Nature*, 315: 592–594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the DNA. During incubation of the plant cell culture with *A. tumefaciens*, the DNA encoding the polypeptide variant is transferred to the plant cell host such that it is transfected, and will, under appropriate conditions, express the DNA. In addition, regulatory and signal sequences compatible with plant cells are available, such as the nopaline synthase promoter and polyadenylation signal sequences. Depicker et al., *J. Mol. Appl. Gen.*, 1: 561 (1982). In addition, DNA segments isolated from the upstream region of the T-DNA 780 gene are capable of activating or increasing transcription levels of plant-expressible genes in recombinant DNA-containing plant tissue. EP 321,196 published 21 Jun. 1989.

However, interest has been greatest in vertebrate cells, and propagation of vertebrate cells in culture (tissue culture) has become a routine procedure in recent years (*Tissue Culture*, Academic Press, Kruse and Patterson, editors [1973]). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36: 59 [1977]); baby hamster kidney cells (BHK, ATCC CCL 10); Chinese hamster ovary cells/-DHFR (CHO, Urlaub and Chasin, *Proc. Natl. Acad. Sci. USA*, 77: 4216 [1980]); mouse sertoli cells (TM4, Mather, *Biol. Reprod.,* 23: 243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL51); TRI cells (Mather et al., *Annals N.Y. Acad. Sci.,* 383: 44–68 [1982]); MRC 5 cells; FS4 cells; and a human hepatoma line (Hep G2).

Host cells are transfected and preferably transformed with the above-described expression or cloning vectors of this invention and cultured in conventional nutrient media modified as appropriate for inducing promoters, selecting transformants, or amplifying the genes encoding the desired sequences. Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene,* 23: 315 (1983) and WO 89/05859 published 29 Jun. 1989. In addition, plants may be transfected using ultrasound treatment as described in WO 91/00358 published 10 Jan. 1991.

For mammalian cells without such cell walls, the calcium phosphate precipitation method of Graham and van der Eb, *Virology,* 52: 456–457 (1978) is preferred. General aspects of mammalian cell host system transformations have been described by Axel in U.S. Pat. No. 4,399,216 issued 16 Aug. 1983. Transformations into yeast are typically carried out according to the method of Van Solingen et al., *J. Bact.,* 130: 946 (1977) and Hsiao et al., *Proc. Natl. Acad. Sci. (USA),* 76: 3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology,* 185: 527–537 (1990) and Mansour et al., *Nature,* 336: 348–352 (1988).

E. Culturing the Host Cells

Prokaryotic cells used to produce the polypeptide variant of this invention are cultured in suitable media as described generally in Sambrook et al., supra.

The mammalian host cells used to produce the polypeptide variant of this invention may be cultured in a variety of media. Commercially available media such as Ham's F-10 (Sigma), F-12 (Sigma), Minimal Essential Medium ([MEM], Sigma), RPMI-1640 (Sigma), Dulbecco's Modified Eagle's Medium ([D-MEM], Sigma), and D-MEM/F-12 (Gibco BRL) are suitable for culturing the host cells. In addition, any of the media described, for example, in Ham and Wallace, *Methods in Enzymology,* 58: 44 (1979); Barnes and Sato, *Anal. Biochem.,* 102: 255 (1980); U.S. Pat. No. 4,767,704; 4,657,866; 4,927,762; 5,122,469; or 4,560,655; U.S. Pat. Re. No. 30,985; WO 90/03430; or WO 87/00195 may be used as culture media for the host cells. Any of these media may be supplemented as necessary with hormones and/or other growth factors (such as insulin, transferrin, aprotinin, and/or epidermal growth factor [EGF]), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of in vitro mammalian cell cultures can be found in *Mammalian Cell Biotechnology: a Practical Approach,* M. Butler, ed. (IRL Press, 1991).

The host cells referred to in this disclosure encompass cells in in vitro culture as well as cells that are within a host animal.

F. Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. USA,* 77: 5201–5205 [1980]), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.,* 75: 734–738 (1980).

Antibodies useful for immunohistochemical staining and/or assay of sample fluids may be either monoclonal or polyclonal, and may be prepared in any mammal. Conveniently, the antibodies may be prepared against a polypeptide variant as described further in Section 4 below.

G. Purification of Polypeptide

If the variant is produced intracellularly, as a first step, the particulate debris, either host cells or lysed fragments, is removed, for example, by centrifugation or ultrafiltration; optionally, the protein may be concentrated with a commercially available protein concentration filter, followed by separating the polypeptide variant from other impurities by one or more steps selected from immunoaffinity chromatography, ion-exchange column fractionation (e.g., on diethylaminoethyl (DEAE) or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the polypeptide, and ethanol or ammonium sulfate precipitation.

Recombinant polypeptide variant produced in bacterial culture may usually be isolated by initial extraction from cell pellets, followed by one or more concentration, salting-out, aqueous ion-exchange, or size-exclusion chromatography steps. Additionally, the recombinant polypeptide variant may be purified by affinity chromatography. Finally, HPLC may be employed for final purification steps. Microbial cells employed in expression of nucleic acid encoding the polypeptide variant may be disrupted by any convenient method, including freeze-thaw cycling, sonication, mechanical disruption, or through the use of cell lysing agents.

A protease inhibitor such as methylsulfonylfluoride (PMSF) may be included in any of the foregoing steps to inhibit proteolysis and antibiotics may be included to prevent the growth of adventitious contaminants.

Within another embodiment, supernatants from systems which secrete recombinant polypeptide variant into culture medium are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise a ligand for the protein, a lectin or antibody molecule bound to a suitable support. Alternatively, an anion-exchange resin may be employed, for example, a matrix or substrate having pendant DEAE groups. Suitable matrices include acrylamide, agarose, dextran, cellulose, or other types commonly employed in protein purification. Alternatively, a cation-exchange step may be employed. Suitable cation exchangers include various insoluble matrices comprising sulfopropyl or carboxymethyl groups. Sulfopropyl groups are particularly preferred.

Finally, one or more RP-HPLC steps employing hydrophobic RP-HPLC media, e.g., silica gel having pendant methyl or other aliphatic groups, may be employed to further purify a polypeptide variant composition. Some or all of the foregoing purification steps, in various combinations, can also be employed to provide a homogeneous recombinant polypeptide variant.

Fermentation of yeast which produce the polypeptide variant as a secreted polypeptide greatly simplifies purification. Secreted recombinant polypeptide variant resulting from a large-scale fermentation may be purified by methods analogous to those disclosed by Urdal et al., *J. Chromatog.*, 296: 171 (1984). This reference describes two sequential, RP-HPLC steps for purification of recombinant human IL-2 on a preparative HPLC column. Alternatively, techniques such as affinity chromatography, may be utilized to purify the polypeptide variant.

Mammalian polypeptide variant synthesized in recombinant culture is characterized by the presence of non-human cell components, including proteins, in amounts and of a character which depend on the purification steps taken to recover the polypeptide variant from culture. These components ordinarily will be from yeast, prokaryotic, or non-human higher eukaryotic origin and preferably are present in innocuous contaminant quantities, on the order of less than about 1% by weight.

H. Covalent Modifications of Polypeptide Variants

Covalent modifications of polypeptide variants are included within the scope of this invention. They may be made by chemical synthesis or by enzymatic or chemical cleavage of the variant polypeptide, if applicable. Other types of covalent modifications of the polypeptide variant are introduced into the molecule by reacting targeted amino acid residues of the polypeptide variant with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_s$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R—N═C═N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W.H. Freeman & Co., San Francisco, pp. 79–86 [1983]), acetylation of the N-terminal amine, and amidation of any C-terminal carboxyl group.

Another type of covalent modification of the polypeptide variant included within the scope of this invention comprises altering the original glycosylation pattern of the polypeptide variant. By altering is meant deleting one or more carbohydrate moieties found in the polypeptide variant, and/or adding one or more glycosylation sites that are not present in the polypeptide variant.

Glycosylation of polypeptide variants is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the polypeptide variant is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original polypeptide variant (for O-linked glycosylation sites). For ease, the polypeptide variant amino acid sequence is preferably altered through changes at the DNA level, particularly by mutating the DNA encoding the polypeptide variant at preselected bases such that codons are generated that will translate into the desired amino acids. The DNA mutation(s) may be made using methods described above.

Another means of increasing the number of carbohydrate moieties on the polypeptide variant is by chemical or enzymatic coupling of glycosides to the polypeptide variant. These procedures are advantageous in that they do not require production of the polypeptide variant in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, *CRC Crit. Rev. Biochem.*, pp. 259–306 (1981).

Removal of any carbohydrate moieties present on the polypeptide variant may be accomplished chemically or enzymatically. Chemical deglycosylation requires exposure of the polypeptide variant to the compound trifluoromethanesulfonic acid, or an equivalent compound. This treatment results in the cleavage of most or all sugars except the linking sugar (N-acetylglucosamine or N-acetylgalactosamine), while leaving the polypeptide variant intact. Chemical deglycosylation is described by Hakimuddin, et al., *Arch. Biochem. Biophys.*, 259: 52 (1987) and by Edge et al., *Anal. Biochem.*, 118: 131 (1981). Enzymatic cleavage of carbohydrate moieties on polypeptide variants can be achieved by the use of a variety of endo- and exo-glycosidases as described by Thotakura et al., *Meth. Enzymol.*, 138: 350 (1987).

Glycosylation at potential glycosylation sites may be prevented by the use of the compound tunicamycin as described by Duskin et al, *J. Biol. Chem.*, 257: 3105 (1982). Tunicamycin blocks the formation of protein-N-glycoside linkages.

Another type of covalent modification of the polypeptide variant comprises linking the polypeptide variant to one of a variety of nonproteinaceous polymers, e.g., polyethylene glycol polypropylene glycol, or polyoxyalkylenes, in the manner set forth in U.S. Pat. No. 4,640,835; 4,496,689; 4,301,144; 4,670,417; 4,791,192 or 4,179,337.

3. Therapeutic Compositions: Administration of Variant

Uses of anti-CD18 variants include anti-Mac1/anti-neutrophil as well as anti-LFA-1 applications. If the polypeptide variant acts as an antibody it may optionally be fused to a second polypeptide and the antibody or fusion thereof may be used to isolate and purify the protein to which it binds from a source such as a CD11 or CD18 antigen. In another embodiment, the invention provides a method for detecting CD11a or CD18 in vitro or in vivo comprising contacting the anti-CD11 a or CD18 antibody fragment variant herein with a sample, especially a serum sample, suspected of containing the CD11a or CD18 and detecting if binding has occurred.

The polypeptide variant herein is also suitably used in quantitative diagnostic assays as a standard or control against which samples containing unknown quantities of the polypeptide variant may be prepared.

Therapeutic formulations of the polypeptide variant for its particular indication are prepared for storage by mixing the polypeptide variant having the desired degree of purity with optional physiologically acceptable carriers, excipients, or stabilizers (*Remington's Pharmaceutical Sciences*, 16th edition, Oslo, A., Ed., [1980]), in the form of lyophilized cake or aqueous solutions. Acceptable carriers, excipients, or stabilizers are non-toxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or non-ionic surfactants such as Tween, Pluronics, or polyethylene glycol (PEG).

Typically, the polypeptide variant used in the method of this invention is formulated by mixing it at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of the variant, but preferably ranges anywhere from about 3 to about 8. Formulation in a buffer at pH about 5–8 is one suitable embodiment.

The polypeptide variant for use herein is preferably sterile. Sterility is readily accomplished by sterile filtration through (0.2 micron) membranes. The polypeptide variant ordinarily will be stored as an aqueous solution, although lyophilized formulations for reconstitution are acceptable.

The variant composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of polypeptide variant to be administered will be governed by such considerations, and, for an LFA-1 antagonist variant, is the minimum amount necessary to prevent, ameliorate, or treat the LFA-1-mediated disorder, including treating rheumatoid arthritis, reducing inflammatory responses, inducing tolerance of immunostimulants, preventing an immune response that would result in rejection of a graft by a host or vice-versa, or prolonging survival of a transplanted graft. The amount of the variant is preferably below the amount that is toxic to the host or renders the host significantly more susceptible to infections.

As a general proposition, the initial pharmaceutically effective amount of the LFA-1 antagonist variant administered parenterally per dose will be in the range of about 0.1 to 20 mg/kg of patient body weight per day, with the typical initial range of LFA-1 antagonist variant used being about 0.3 to 15 mg/kg/day.

As noted above, however, these suggested amounts of LFA-1 antagonist variant are subject to a great deal of therapeutic discretion. The key factor in selecting an appropriate dose and scheduling is the result obtained, as indicated above. For example, relatively higher doses may be needed initially for the treatment of ongoing and acute graft rejection, or at a later stage for the treatment of acute rejection, which is characterized by a sudden decline in graft function.

Where the subsequent dosing is less than 100% of initial dosing, it is calculated on the basis of daily dosing. Thus, for example, if the dosing regimen consists of daily injections of 2 mg/kg/day for 2 weeks followed by a biweekly dose of 0.5 mg/kg/day for 99 days, this would amount to a subsequent dose of about 1.8% of the initial dose, calculated on a daily basis (i.e., 2/day/100%=0.5/14 days/x %, x=~1.8%). Preferably, the subsequent dosing is less than about 50%, more preferably, less than about 25%, more preferably, less than about 10%, still more preferably, less than about 5%, and most preferably, less than about 2% of the initial dosing of LFA-1 antagonist variant.

To obtain the most efficacious results for the LFA-1 antagonist variant, depending on the disorder, the initial dosing is given as close to the first sign, diagnosis, appearance, or occurrence of the disorder as possible or during remissions of autoimmune disorders. Preferably the initial dosing begins before exposure to antigen, as in the case with transplanted grafts. Furthermore, when the initial dosing is prior to or substantially contemporaneous with exposure to antigen, it is preferred that the subsequent dosing is carried out for a longer period of time than the initial dosing, particularly for transplants, and that it be a continuous intermittent maintenance dose that need not be continuous for the life of the patient.

The preferred scheduling for the LFA-1 antagonist variant is that the initial dosing (i.e., administered before or at the time of the undesired immune response at a dose administered no less frequently than daily up to and including continuously by infusion) and the subsequent dosing is a dose administered periodically no more than about once a week. More preferably, depending on the specific disorder, and particularly for transplantation, the initial daily dosing is administered for at least about one week, preferably at least about 2 weeks, after the exposure to antigen, e.g., graft, or initiation of an acute immune response (as in autoimmune disorders), and the subsequent dosing is administered no more than once biweekly (preferably once biweekly) for at least about 5 weeks, preferably for at least about 10 weeks, after the initial dosing is terminated.

In another preferred embodiment, particularly if the antagonist variant is a Fab or (Fab')$_2$ of anti-CD11a or anti-CD18 antibodies, initial dosing terminates from about 1 day to 4 weeks after transplantation has occurred, more preferably from about 1 week to 3 weeks, more preferably from about 2 weeks to 3 weeks, and commences from about 1 week before transplantation occurs up to about simultaneously with the transplantation.

The polypeptide variant is administered by any suitable means, including parenteral, subcutaneous, intraperitoneal, intrapulmonary, and intranasal, and, if desired for local immunosuppressive treatment, intralesional administration (including perfusing or otherwise contacting the graft with the antagonist before transplantation). Parenteral infusions include intramuscular, intravenous, intraarterial, intraperitoneal, or subcutaneous administration. In addition, the LFA-1 antagonist variant is suitably administered by pulse infusion, particularly with declining doses of the LFA-1 antagonist variant. Preferably the dosing of such variant is given by injections, most preferably intravenous or subcutaneous injections, depending in part on whether the administration is brief or chronic.

The polypeptide variant herein need not be, but is optionally formulated with one or more agents currently used to prevent or treat the disorder in question. For example, in rheumatoid arthritis, an LFA-1 antagonist variant may be given in conjunction with a glucocorticosteroid. In addition, T cell receptor peptide therapy is suitably an adjunct therapy to prevent clinical signs of autoimmune encephalomyelitis. Offner et al., *Science,* 251: 430–432 (1991). For transplants, the LFA-1 antagonist variant may be administered concurrently with or separate from an immunosuppressive agent as defined above, e.g., cyclosporin A, to modulate the immunosuppressant effect. The effective amount of such other agents depends on the amount of LFA-1 antagonist variant present in the formulation, the type of disorder or treatment, and other factors discussed above. These are generally used in the same dosages and with administration routes as used hereinbefore or about from 1 to 99% of the heretofore employed dosages.

The various autoimmune disorders described above are treated with LFA-1 antagonist variants in such a fashion as to induce immune tolerance to the self antigen under attack as a result of the disorder. In this regard, autoimmune disorders resemble host versus graft rejection and are treated with LFA-1 antagonist variants in analogous fashion. However, in these disorders the patient is already mounting an immune response to the target antigen, unlike the case with transplants prior to grafting. Thus, it is desirable to first induce and maintain a transient state of immunosuppression by conventional methods in such patients, e.g., by the conventional use of cyclosporin A or other conventional immunosuppressive agents (alone or together with LFA-1 antagonist variant), or to monitor the patient until the occurrence of a period of remission (an absence or substantial lessening of pathological or functional indicia of the autoimmune response).

Preferably, transient immunosuppression is induced by T cell depletion using conventional therapy. This is then followed by the administration of the LFA-1 antagonist variant in order to prevent rebound when the immunosuppressive inducing agent is withdrawn or when remission otherwise would abrogate. Alternatively, the remission patient's condition is closely monitored for signs of flare, and immediately upon the initial functional or biochemical appearance of flare the initial dosing regimen is started and continued until the flare subsides. The LFA-1 antagonist variant administration during this period constitutes the initial dose described elsewhere herein.

In the case of autoimmune disorders the initial dose will extend about from 1 week to 16 weeks. Thereafter, the lower dose maintenance regimen of LFA-1 antagonist variant is administered in substantially the same fashion as set forth herein for the amelioration of graft or host rejection, although in some instances it is desirable to extend the subsequent or sustaining dose for lengthier periods than with grafts. In an embodiment of this invention, if an antigen or a composition containing the antigen is known to be responsible for the autoimmune response then the antigen is administered to the patient (optionally with IL-1 and/or gamma interferon) after the initial LFA-1 antagonist variant dose and the antagonist variant dose maintained thereafter in order to suppress the regeneration of an autoimmune response against the antigen while minimally immunosuppressing the patient's response to other antigens.

The patient optimally will be isolated, preferably in an aseptic environment such as is currently used in transplant practice, at the time of initial treatment with LFA-1 antagonist variant. The patient should be free of any infection. It is not necessary to sustain these conditions during the maintenance dose, and in fact this is one of the advantages of this invention, i.e., that the patient is able to mount a substantially normal immune response to ambient antigens (other than the graft or self antigen) while being treated with the maintenance dosing.

The invention herein is particularly amenable to prolonging survival and increasing tolerance of transplanted grafts. The transplants are optionally functionally monitored systematically during the critical postoperative period (the first three months) using any suitable procedure. One such procedure is radionuclide intravenous angiography using 99Tcm-pertechnetate, as described by Thomsen et al., *Acta Radiol.*, 29: 138–140 (1988). In addition, the method herein is amenable to simultaneous, multiple organ perfusion and transplantation. Toledo-Pereyra and MacKenzie, *Am. Surg.*, 46: 161–164 (1980).

In some instances, it is desirable to modify the surface of the graft so as to provide positively or negatively charged groups, as by using a suitable amino acid or polymer or by attaching a physiologically acceptable source of charged functional groups. For example, a negatively charged surface is appropriate for blood vessels to diminish blood clotting. It also is desirable in certain circumstances to render the surface hydrophobic or hydrophilic by coupling, e.g., phenylalanine, serine or lysine to the surface. An immunosuppressive agent particularly effective for these surface modifications is glutaraldehyde.

As mentioned above, before transplantation an effective amount of the LFA-1 antagonist variant is optionally administered to induce tolerance of the graft. The same dose and schedule as used for initial post-transplantation may be employed. Furthermore, prior to transplantation the graft is optionally contacted with a TGF-β composition as described in U.S. Pat. No. 5,135,915, the disclosure of which is incorporated by reference. Briefly, the contact suitably involves incubating or perfusing the graft with the composition or applying the composition to one or more surfaces of the graft. The treatment generally takes place for at least one minute, and preferably from 1 minute to 72 hours, and more preferably from 2 minutes to 24 hours, depending on such factors as the concentration of TGF-β in the formulation, the graft to be treated, and the particular type of formulation. Also as noted, the graft is simultaneously or separately perfused with LFA-1 antagonist variant. Perfusion is accomplished by any suitable procedure. For example, an organ can be perfused via a device that provides a constant pressure of perfusion having a pressure regulator and overflow situated between a pump and the organ, as described by DD 213,134 published Sep. 5, 1984. Alternatively, the organ is placed in a hyperbaric chamber via a sealing door and perfusate is delivered to the chamber by a pump that draws the fluid from the reservoir while spent perfusate is returned to the reservoir by a valve, as described in EP 125,847 published Nov. 21, 1984.

After the graft is treated, it is suitably stored for prolonged periods of time or is used immediately in the transplant procedure. Storage life can be enhanced as described above by using a blood substitute in the formulation (e.g., perfluorochemical emulsion), or by perfusing the graft with a formulation of a TGF-β containing chilled isotonic agent and anticoagulant followed by glycerol to allow for freezing of removed organs with no destruction of the cells, as described in JP 60061501 published Apr. 9, 1985. In addition, the organs can be preserved with known perfusion fluids (containing TGF-β and/or LFA-1 antagonist as noted) while the organs are cooled to freezing temperatures, to preserve the organ semi-permanently without cell necrocytosis, as described by U.S. Pat. Nos. 4,462,215 and 4,494,385.

Respecting cardiac transplants specifically, Parent et al., *Cryobiology,* 18: 571–576 (1981) reports that cold coronary perfusion prior to transplantation at 5° C. increases protection of the homograft during the initial period of implantation. Any of these procedures, or others, are within the scope of this invention if deemed necessary for graft preservation.

Before transplantation; the graft is preferably washed free of the TGF-β composition, as by soaking it in a physiological saline solution or by other means appropriate for this purpose. It is not desirable to remove the LFA-1 antagonist variant prior to transplantation.

Also, prior to transplantation, the host is optionally given one or more donor-specific blood transfusions to aid in graft survival. An alternative procedure is to subject the host to total lymphoid irradiation prior to or after the transplantation operation. Any other pre-transplant procedures that would be beneficial to the particular transplant recipient can be performed as part of the method of this invention.

4. Antibody Preparation (where Variant is Antibody-derived)

(i) Starting Materials and Methods

Immunoglobulins (Ig) and certain variants thereof are known and many have been prepared in recombinant cell culture. For example, see U.S. Pat. No. 4,745,055; EP 256,654; EP 120,694; EP 125,023; EP 255,694; EP 266,663; WO 88/03559; Faulkner et al., *Nature,* 298: 286 (1982); Morrison, *J. Immun.,* 123: 793 (1979); Koehler et al., *Proc. Natl. Acad. Sci. USA,* 77: 2197 (1980); Raso et al., *Cancer Res.,* 41: 2073 (1981); Morrison et al., *Ann. Rev. Immunol.,* 2: 239 (1984); Morrison, *Science,* 229: 1202 (1985); and Morrison et al., *Proc. Natl. Acad. Sci. USA,* 81: 6851 (1984). Reassorted immunoglobulin chains are also known. See, for example, U.S. Pat. No. 4,444,878; WO 88/03565; and EP 68,763 and references cited therein. The immunoglobulin moiety in the polypeptide variants of the present invention may be obtained from IgG-1, IgG-2, IgG-3, or IgG4 subtypes, IgA, IgE, IgD, or IgM, but preferably from IgG-1 or IgG-3.

(ii) Polyclonal Antibodies

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and R1 are different alkyl groups.

Animals are immunized against the antigen, immunogenic conjugates, or derivatives by combining 1 mg or 1 µg of the peptide or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal antibodies

Monoclonal antibodies are obtained from a population of substantially homogeneous antibodies, ie., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler and Milstein, *Nature,* 256: 495 (1975), or may be made by recombinant DNA methods (Cabilly et al., supra).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice,* pp. 59–103 [Academic Press, 1986]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, *J. Immunol.,* 133: 3001 [1984]; Brodeur et al., *Monoclonal Antibody Production Techniques and Applications,* pp. 51–63 [Marcel Dekker, Inc., New York, 1987]).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson and Pollard, *Anal. Biochem.,* 107: 220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.,* 5: 256–262 (1993) and Plückthun, *Immunol. Revs.,* 130: 151–188 (1992).

In a further embodiment, antibodies or antibody fragments can be isolated from antibody phage libraries generated using the techniques described in McCafferty et al., *Nature,* 348: 552–554 (1990), using the proper antigen such as CD11a, CD18, IgE, or HER-2 to select for a suitable antibody or antibody fragment. Clackson et al., *Nature*, 352: 624–628 (1991) and Marks et al., *J. Mol. Biol.*, 222: 581–597 (1991) describe the isolation of murine and human antibodies, respectively, using phage libraries. Subsequent publications describe the production of high affinity (nM range) human antibodies by chain shuffling (Mark et al., *Bio/Technology*, 10: 779–783 [1992]), as well as combinatorial infection and in vivo recombination as a strategy for constructing very large phage libraries (Waterhouse et al., *Nuc. Acids. Res.*, 21: 2265–2266 [1993]). Thus, these techniques are viable alternatives to traditional monoclonal antibody hybridoma techniques for isolation of "monoclonal" antibodies.

The DNA also may be modified, for example, by substituting the coding sequence for human heavy- and light-chain constant domains in place of the homologous murine sequences (Cabilly et al., supra; Morrison, et al., *Proc. Nat. Acad. Sci.*, 81: 6851 [1984]), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

For diagnostic applications, the variants herein derived from antibodies typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$; a fluorescent or chemiluminescent compound, such as fluorescein isothiocyanate, rhodamine, or luciferin; radioactive isotopic labels, such as, e.g., $^{125}I$, $^{32}P$, $^{14}C$, or $^3H$; or an enzyme, such as alkaline phosphatase, beta-galactosidase, or horseradish peroxidase.

Any method known in the art for separately conjugating the polypeptide variant to the detectable moiety may be employed, including those methods described by Hunter et al., *Nature*, 144: 945 (1962); David et al., *Biochemistry*, 13: 1014 (1974); Pain et al., *J. Immunol. Meth.*, 40: 219 (1981); and Nygren, *J. Histochem. and Cytochem.*, 30: 407 (1982).

(iv) Humanized and human antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321: 522–525 [1986]; Riechmann et al., *Nature*, 332: 323–327 [1988]; Verhoeyen et al., *Science*, 239: 1534–1536 [1988]), by substituting rodent CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151: 2296 [1993]; Chothia and Lesk, *J. Mol. Biol.*, 196: 901 [1987]). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89: 4285 [1992]; Presta et al., *J. Immnol.*, 151: 2623 [1993]).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90: 2551–255 (1993); Jakobovits et al., *Nature*, 362: 255–258 (1993); Bruggermann et al., *Year in Immuno.*, 7: 33 (1993). Human antibodies can also be produced in phage-display libraries (Hoogenboom and Winter, *J. Mol. Biol.*, 227: 381 [1991]; Marks et al., *J. Mol. Biol.*, 222: 581 [1991]).

(v) Bispecific Antibodies

Bispecific antibodies (BsAbs) are antibodies that have binding specificities for at least two different antigens. Bispecific antibodies can be derived from full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein and Cuello, *Nature*, 305: 537–539 [1983]). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published 13 May 1993, and in Traunecker et al., *EMBO J.*, 10: 3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies see, for example, Suresh et al., *Methods in Enzymology*, 121:210 (1986).

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the BsAb. The BsAbs produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217–225 (1992) describe the production of a fully humanized BsAb F(ab')$_2$ molecule. Each Fab' fragment was separately secreted from *E. coli* and subjected to directed chemical coupling in vitro to form the BsAb. The BsAb thus formed was able to bind to cells overexpressing the HER2 receptor and normal human T cells, as well as trigger the lytic activity of human cytotoxic lymphocytes against human breast tumor targets. See also Rodrigues et al., *Int. J. Cancers*, (Suppl.) 7: 45–50 (1992).

Various techniques for making and isolating BsAb fragments directly from recombinant cell culture have also been described. For example, bispecific F(ab')$_2$ heterodimers have been produced using leucine zippers, Kostelny et al., *J. Immunol.*, 148(5): 1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Natl. Acad. Sci. (USA)*, 90: 6444–6448 (1993) has provided an alternative mechanism for making BsAb fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making BsAb fragments by the use of single-chain Fv (sFv) dimers has also been reported. See Gruber et al., *J. Immunol.*, 152: 5368 (1994). These researchers designed an antibody which comprised the $V_H$ and $V_L$ domains of a first antibody joined by a 25-amino-acid-residue linker to the $V_H$ and $V_L$ domains of a second antibody. The refolded molecule bound to fluorescein and the T-cell receptor and redirected the lysis of human tumor cells that had fluorescein covalently linked to their surface.

5. Uses of Antibody Variants

Variant antibodies are useful in diagnostic assays for an antigen of interest, e.g., its production in specific cells, tissues, or serum. The variant antibodies are labeled in the same fashion as described above and/or are immobilized on an insoluble matrix. In one embodiment of an antigen-binding assay, an antibody composition that binds to the antigen is immobilized on an insoluble matrix, the test sample is contacted with the immobilized variant antibody composition to adsorb the antigen, and then the immobilized antigen is contacted with variant antibodies specific for the antigen, as determined by unique labels such as discrete fluorophores or the like. By determining the presence and/or amount of each unique label, the relative proportion and amount of the antigen can be determined.

The variant antibodies of this invention are also useful in passively immunizing patients.

The variant antibodies also are useful for the affinity purification of an antigen of interest from recombinant cell culture or natural sources.

Suitable diagnostic assays for an antigen and its variant antibodies are well known per se. In addition to the bioassays described in the examples below wherein the candidate variant is tested to see if it has appropriate biological activity and increased half-life, competitive, sandwich and steric inhibition immunoassay techniques are useful. The competitive and sandwich methods employ a phase-separation step as an integral part of the method while steric inhibition assays are conducted in a single reaction mixture. Fundamentally, the same procedures are used for the assay of the antigen and for substances that bind the antigen, although certain methods will be favored depending upon the molecular weight of the substance being assayed. Therefore, the substance to be tested is referred to herein as an analyte, irrespective of its status otherwise as an antigen or variant antibody, and proteins that bind to the analyte are denominated binding partners, whether they be antibodies, cell-surface receptors, or antigens.

Analytical methods for the antigen or its variant antibodies all use one or more of the following reagents: labeled analyte analogue, immobilized analyte analogue, labeled binding partner, immobilized binding partner, and steric conjugates. The labeled reagents also are known as "tracers."

Immobilization of reagents is required for certain assay methods. Immobilization entails separating the binding partner from any analyte that remains free in solution. This conventionally is accomplished by either insolubilizing the binding partner or analyte analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the partner or analogue afterward, e.g., by immunoprecipitation.

Other assay methods, known as competitive or sandwich assays, are well established and widely used in the commercial diagnostics industry.

Competitive assays rely on the ability of a tracer analogue to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results to quantitatively determine the amount of analyte present in the test sample. These assays are called ELISA systems when enzymes are used as the detectable markers.

Another species of competitive assay, called a "homogeneous" assay, does not require a phase separation. Here, a conjugate of an enzyme with the analyte is prepared and used such that when anti-analyte binds to the analyte the presence of the anti-analyte modifies the enzyme activity. In this case, the antigen or its immunologically active fragments are conjugated with a bifunctional organic bridge to an enzyme such as peroxidase. Conjugates are selected for use with anti-polypeptide so that binding of the anti-polypeptide inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore.

Sandwich assays particularly are useful for the determination of polypeptide variants or polypeptide variant antibodies. In sequential sandwich assays an immobilized binding partner is used to adsorb test sample analyte, the test sample is removed as by washing, the bound analyte is used to adsorb labeled binding partner, and bound material is then separated from residual tracer. The amount of bound tracer is directly proportional to test sample analyte. In "simultaneous" sandwich assays the test sample is not separated before adding the labeled binding partner. A sequential sandwich assay using a monoclonal antibody as one antibody and a polyclonal antibody as the other is useful in testing samples for antigen activity.

The foregoing are merely exemplary diagnostic assays for the polypeptide variant and variant antibodies. Other methods now or hereafter developed for the determination of these analytes are included within the scope hereof, including the bioassays described above.

The following examples are offered by way of illustration and not by way of limitation. The disclosures of all citations in the specification are expressly incorporated herein by reference.

EXAMPLE 1

Methods

Plasmid Construction

The template plasmid, pH52, used for constructing the Fabs (hereafter referred to as Fab) employed in this example was derived from the plasmid pB0475 described by Cunningham et al., *Science* 243: 1330–1336 (1989). Two BamHI sites flanking the F1 origin were removed from pB0475 and DNA coding for anti-CD18 Fab H52, version OZ (Eigenbrot et al., *Proteins*, 18: 49–62 [1994]) was substituted for DNA coding for human growth hormone using the EcoRV and SphI sites. Hence, pH52 contains DNA coding for anti-CD18 Fab H52 (version OZ), the STII signal peptides of the light and heavy chain, the alkaline phosphatase promoter region, an M13 helper phage region, and ampicillin-resistance. Fab variants were constructed by Kunkel mutagenesis (Kunkel, *Proc. Natl. Acad. Sci. U.S.A.*, 82: 488–492 [1985]) of pH52 using the following oligonucleotides:

```
oligo V1A 5' GTGACCGTGCCTCACCAGAGCTTGGGCAC3'              (SEQ ID NO: 12)
changes Ser195-Ser196 to His195-Gln196 oligo V1B 5' TGGCACCCTCCCCTAAGAACTCGAGCATGATCAGC-        (SEQ ID NO: 13)
AACACACCGGCCCTGGGC3'
changes Ser127-Ser-Lys-Ser-Thr-Ser-Gly-Gly-Thr-Ala-Ala139   (SEQ ID NO: 14)
to Ser127-Pro-Lys-Asn-Ser-Ser-Met-Ile-Ser-Asn-Thr-Pro-Ala139 (SEQ ID NO: 15)

oligo V1C 5' TGGCACCCTCCAAATCGAGCATCACAGCGGCCCT3'       (SEQ ID NO: 16)
changes Ser127-Ser-Lys-Ser-Thr-Ser-Gly-Gly-Thr137          (SEQ ID NO: 17)
to Ser127-Lys-Ser-Ser-Ile-Thr137                            (SEQ ID NO: 18)

oligo V2 5' TGGTGACCGTGATCTCGAGCCACTTGGGCCAGCAGACCTACATC3' (SEQ ID NO: 19)
changes Val193-Pro-Ser-Ser-Ser-Leu-Gly-Thr-Gln203          (SEQ ID NO: 20)
to Val193-Ile-Ser-Ser-His-Leu-Gly-Gln-Gln203               (SEQ ID NO: 21)
```

Amino acid residue numbers are according to the numbering system described in Kabat et al., supra, *NIH Publ. No. 91-3242*, Vol. I, pages 647–669 (1991).

Fab v1 incorporated oligos V1A and V1C; Fab v1b incorporated oligos V1A and V1B; Fab v2 incorporated oligo V2. Plasmids coding for Fab v1, Fab v1b, and Fab v2 were selected and the DNA sequences checked using dideoxynucleotide sequencing (Sequenase™ protocol, United States Biochemical). F(ab')₂ constructs were made by inserting DNA coding for the IgG1 hinge region followed by a 'leucine zipper' at the C-terminus of the H52 heavy constant domain. The inserted amino acid sequence was:

chloride (Sigma™ A9434), 0.075 g KCl (Sigma™ P5405), 4.09 g NaCl (Sigma™ S3014), 120.0 mL of 1 M triethanolamine pH 7.4, qs to 1.0 L Super-Q™ Water, as well as 1 M triethanolamine pH 7.4 consisting of 133.21 mL triethanolamine, Liquid (Sigma™ T1377) and 950 mL Super-Q™ Water, pH to 7.4 with HCl (Mallinckrodt™ 2612), qs to 1.0 L Super-Q™ Water. This is filtered through a 0.1 μm Sealkleen™ filter and stored at 2–8° C. The expiration period is 6 months.

The cells were spun in a 1-L centrifuge bottle at 3000 rpm for 30 minutes, the supernatant was decanted and the pel-

```
CPPCPAPELLGGRMKQLEDKVEELLSKNYHLENEVARLKKLVGER (SEQ ID NO: 22).
```

Another set of Fab versions is based on Fab v1b, i.e., the variant which showed longer half life, using the following oligonucleotides:

leted cells were frozen for 1 hour. The pellet was resuspended in 10 mL of cold TE buffer (10 mM TRIS, 1 mM EDTA, pH 7.6) with 100 μL 0.1 M benzamidine (Sigma)

```
oligo V1D 5' TCGAGCATGATCTCTAGAACACCGGCCC3'              (SEQ ID NO: 23)
changes Asn136 to Arg136 oligo V1E 5' GCCTCACCAGAACCTAGGCACCAAGACCTACATCTG3'     (SEQ ID NO: 24)
changes Ser197 to Asn197 and Gln203 to Lys203 oligo V1F 5' GCCTCACCAGAACTTAAGCGACGGAAAGACCTACATCTGC3' (SEQ ID NO: 25)
changes Gln196-Ser-Leu-Gly-Thr-Gln-Thr204                (SEQ ID NO: 26)
to Gln196-Asn-Leu-Ser-Asp-Gly-Lys-Thr204                 (SEQ ID NO: 27)

oligo V1G 5' GCCTCACCAGAATATTACAGATGGCAAGACCTACATCTGC3' (SEQ ID NO: 28)
changes Gln196-Ser-Leu-Gly-Thr-Gln-Thr204                (SEQ ID NO: 29)
to Gln196-Asn-Ile-Ser-Asp-Gly-Lys-Thr204                 (SEQ ID NO: 30)
```
Fab v3 incorporates oligo V1D; Fab v4 incorporates oligo V1E; Fab v5 incorporates oligo V1F; and Fab v6 incorporates oligo V1G.

Expression of DNA Encoding the Variants

For each variant, plasmid DNA was transformed into *E. coli*. The transformants were then plated on Luria Broth (LB) plates containing 5 μg/mL carbenicillin and incubated at 37° C. overnight. A single colony was inoculated into 5 mL [LB+5 μg/mL carbenicillin] and grown for 6–7 hours at 37° C. The 5-mL culture was then added to 500 mL AP5 minimal media in a 2-L baffled flask and grown for 16 hours at 37° C.

AP5 minimal media is made as follows: Per 1 liter is added 1.5 g glucose (Sigma™ G-7021), 2.2 g casamino acids technical (Difco™ 0231-01-0), 0.3 g yeast extract certified (Difco™ 0127-01-7), 0.19 g MgSO₄ anhydrous or 0.394 g MgSO₄·7H₂O (Sigma™ M2773), 1.07 g ammonium added. The resuspended pellet was agitated on ice for 1 hour, spun at 18,000 rpm for 15 minutes, and the supernatant decanted and held on ice.

The supernatant was then passed over a Protein G-Sepharose™ Fast Flow (Pharmacia) column [0.5 mL bed volume] previously equilibrated by passing 10 mL TE buffer through the column. The column was then washed with 10 mL TE buffer, and the Fab eluted with 2.5 mL 100 mM acetic acid, pH 2.8, into a tube containing 0.5 mL TRIS, pH 8.0. The eluant was concentrated in a Centricon-30™ (Amicon) centrifuge to 0.5 mL, 2 mL phosphate-buffered saline was added to concentrated eluant, and the resulting mixture was re-concentrated to 0.5 mL. SDS-PAGE gels were run to ascertain that protein had been produced.

Analytical Methods Used During Purification Procedure of Anti-CD11/CD18 Fab Variants and F(ab')$_2$ Antibody Fragment SDS polyacrylamide gel electrophoresis (SDS-PAGE) and two different high performance liquid chromatography (HPLC) methods were used to analyze the products obtained in each step of the purification process. The HPLC methods used include reverse-phase chromatography and cation-exchange chromatography, which were performed on a WATERS™ HPLC system.

Reverse-phase chromatography was carried out on a reverse-phase PLRP-S™ 4.6×50 mm column, 8-mm particle size (Polymer Laboratories, Shropshire, UK), maintained at 50° C. The proteins were eluted using an increasing linear gradient from 31% B to 41% B. Buffer A contained 0.1% trifluoroacetic acid in deionized water, and Buffer B contained 0.1% trifluoroacetic acid in HPLC-grade acetonitrile. The flow rate was maintained at 2 mL/min, and the protein profile was monitored at 214 nm.

Analysis by cation-exchange chromatography was carried out on a Bakerbond carboxy-sulfon (CSX)™ 50×4.6 mm column (J. T. Baker Phillipsburg, N.J.), maintained at 55° C. The proteins were eluted using an increasing linear gradient from pH 6.0 to pH 8.0 at a flow rate of 2 mL/min using a detection wavelength of 280 nm. Buffer A contained 16 mM each of HEPES/PIPES/MES, pH 6.0, and Buffer B contained 16 mM each of HEPES/PIPES/MES, pH 8.0. For the separation of the different Fab variants, a linear gradient was run for 22 min from 25% B to 56% B. For the separation of the Zipper-F(ab')2 and F(ab')2 antibody fragments, the linear gradient was run from 40% B to 100% B in 22 minutes.

SDS-PAGE analysis was carried out on precast Novex™ gels (Novex, San Diego, Calif.). The proteins were stained using the Morrissey silver stain method. Morrissey, *Anal. Biochem.*, 117: 307–310 (1981).

Purification of Anti-CD11/CD18 Fab Antibody Fragment and Fab Variants

The anti-CD11/CD18 Fab antibody fragment and the different Fab variants were isolated using the same extraction and purification scheme.

Extraction

Frozen cell pellets (100 g) were re-suspended at room temperature in 120 mM MES buffer, pH 6.0, containing 5 mM EDTA (5 ml of buffer per g of cell pellet) and completely disrupted by three passages through a microfluidizer (Microfluidics Corporation, Newton, Mass.). The homogenate was adjusted to 0.25% (v/v) polyethyleneimine (PEI) and the solid debris was removed by centrifugation (7280×g, 30 min, 4° C.).

ABX Chromatography

The supernatant containing the antibody fragment was diluted to a conductivity of 2.5 millisiemens with purified water, filtered through a 0.22 micron filter (Suporcap-50™, Gelman Sciences, Ann Arbor, Mich.), and then loaded onto a 1.6×9.5 cm Bakerbond ABX column (J. T. Baker, Phillipsburg, N.J.) equilibrated in 50 mM MES/5 mM disodium EDTA, pH 6.0 (Buffer A). The effluent was UV monitored at 280 nm. After loading, the column was washed with Buffer A until the UV trace returned to baseline. Antibody fragments were eluted with a 20-column-volume gradient from 0 to 100 mM ammonium sulfate in buffer A. Fractions were analyzed on a cation-exchange column as described in the Analytical Methods section above and pooled accordingly.

SP Sepharose High Performance (SPHP) Chromatography

The ABX pool was diluted with water for injection (WFI) to a conductivity of less than 4 mS and loaded onto a SPHP 1.6×9.2 cm column (Pharmacia Biotech Inc., Piscataway, N.J.), equilibrated with 25 mM MOPS buffer, pH 6.9. Separation was achieved by a 20-column-volume linear gradient from 0 to 200 mM sodium acetate in 25 mM MOPS buffer, pH 6.9. Fractions were analyzed by CSX HPLC and SDS-PAGE as described in the Analytical Methods section above and pooled accordingly.

Formulation

The SPHP pools containing the antibody fragments were concentrated to 5 mg/mL using Amicon stir cells and YM10 membrane filters (Amicon, Inc. Beverly, Mass.). The purified and concentrated antibody samples were buffer-exchanged into phosphate buffer saline (PBS) by gel permeation chromatography on a Sephadex™ G25 (Pharmacia Biotech Inc. Piscataway, N.J.) column.

Endotoxin Determinations

Endotoxin determinations were performed with the *Limulus* amoebocyte lysate test (Associates of Cape Cod Inc., Woods Hole, Mass.). Samples containing less than 2 endotoxin units (Eu) per mg of protein were used in the pharmacokinetic studies.

Purification of the Anti-CD11/CD18 F(ab')$_2$ Antibody Fragment

The F(ab')$_2$ fragment was initially purified by ABX chromatography as a leucine zipper (Fab')$_2$ variant [zipper-F(ab')$_2$]. This construct was engineered by adding a leucine zipper domain after the hinge region of the H52 heavy chain. After purification, the leucine zipper domain was cleaved by pepsin digestion after which the F(ab')$_2$ was purified by SPHP and Phenyl Toyopearl™ chromatography as described below.

Extraction and ABX Chromatography of Zipper-F(ab')$_2$ Antibody Fragment

Extraction and ABX chromatography of the zipper-F (ab')$_2$ antibody fragment was carried out as described above for the Fab antibody fragment variants.

Pepsin Digestion of Zipper-F(ab')$_2$ Antibody Fragment

The ABX-purified Zipper-F(ab')$_2$ was treated with pepsin to remove the leucine zipper portion of the molecule to yield the F(ab') antibody fragment. The ABX purified sample was concentrated on Amicon stir cells to 5 mg/mL and then diluted 1:3.5 with 100 mM sodium citrate buffer, pH 3.5. To this solution, pepsin (1 mg/mL) dissolved in 100 mM sodium citrate buffer, pH 3.5, was added at a pepsin-to-protein ratio of 1:12. After 4 hours at room temperature, the mixture's pH was raised to pH 6.4 with 10% NaOH.

SPHP Chromatography of Pepsin-Treated Zipper-F(ab')$_2$ Antibody Fragment

Purification of the F(ab')$_2$ antibody fragment from the leucine zipper domain and undesired antibody fragments was accomplished by SPHP chromatography as described above for the Fab antibody fragment variants.

Phenyl Toyopearl™ Chromatography of SPHP-purified F(ab')$_2$ Antibody Fragment

The SPHP-purified F(ab')$_2$ pool was made 1.5 M in ammonium sulfate by adding solid ammonium sulfate. The conditioned pool was then loaded onto a Phenyl Toyopearl™ 650M (Tosohaas, Montgomeryville, Pa.) 1.6×10 cm column equilibrated with 1.5 M ammonium sulfate, 50 mM sodium acetate, pH 5.4 (Buffer A). A 20-column-volume gradient was runned from 70% Buffer A to 100% 0.15 M ammonium sulfate in 50 mM sodium acetate, pH 5.4 (Buffer B). The fractions were analyzed by reverse phase and CSX HPLC and SDS-PAGE as described in the Analytical Methods section above.

Formulation of F(ab')$_2$ Antibody Fragment and Endotoxin Measurements

Formulation of the purified F(ab')$_2$ antibody fragment was performed as described above for the Fab antibody fragment variants. After endotoxin determinations, samples containing less than 2 Eu per mg of protein were used in the pharmacokinetic studies set forth below.

Pharmacokinetic Study of Anti-CD11/18 Constructs in Mice after Intravenous Administration The objective of this single-dose pharmacokinetic study of five humanized huH52 anti-CD18 antibody fragments (constructs) in mice was to determine if non-specific clearance of antibody fragments is affected by alterations to amino acids in the constant domain. Serum samples were collected from male CD1 mice over a 24-hour period and human anti-CD18 serum concentrations were measured by ELISA.

The anti-CD18 antibody fragments investigated were derived from *E.-coli*-produced recombinant humanized monoclonal Fab antibody fragments as described above. The Fab fragment and the construct in which two Fab' subunits were joined together by two disulfide bonds were investigated. Lastly, three new versions of the original Fab were constructed by altering amino acids in the constant domain. See the Study Design table below for further description of the constructs.

The construct antigen-binding sites are directed against the CD18 subunit of the CD11/CD18 glycoprotein complex on the surface of leukocytes. These antibody fragments are chimpanzee and human-specific; therefore, the serum pharmacokinetic information obtained in mice provides a description of the non-specific clearance of the fragments.

Because linear pharmacokinetics were expected in this study, a single-dose level of 2 mg/kg was chosen rather than multiple-dose levels.

Study Designs[a]

| Group Number | Construct ID | Construct Description |
| --- | --- | --- |
| 1 | Fab | Fab fragment alone |
| 2 | Double disulfide | Two Fab' subunits joined with a double disulfide bond |
| 3 | Fabv1 | new version 1 of the original Fab constructed by altering amino acids in the constant domain |
| 4 | Fabv1B | new version 1B of the original Fab constructed by altering amino acids in the constant domain |
| 5 | Fabv2 | new version 2 of the original Fab constructed by altering amino acids in the constant domain |

[a]Each group consisted of 20 male mice; each mouse received a 2 mg/kg dose.

The pharmacokinetics of the five antibody constructs were studied in male Crl:CD-1® (ICR)BR VAF/Plus® mice (approximately 20–30 g). Five groups, each consisting of twenty mice, received an intravenous bolus dose of 2 mg/kg via the tail vein. Blood samples were collected at 5 and 30 minutes, 1, 2, 4, 8, 12, 16, 20, and 24 hours post-dose. Serum was harvested and concentrations of the antibody fragments were determined in a MAC-1 capture ELISA as follows:

96-Well microtiter plates were coated overnight with murine anti-CD18 monoclonal antibody. After overnight incubation at 4° C., plates were washed three times with ELISA wash buffer and blocked for 1 hour with ELISA diluent. ELISA wash buffer is phosphate-buffered saline (PBS)/0.05% Polysorbate™ 20. This buffer is prepared per liter as 50 mL 20×PBS/1.0% Polysorbate™ 20 (a mixture obtained by dissolving 160 g NaCl, 4.0 g KCl, 22.6 g Na$_2$HPO$_4$, and 4.0 g KH$_2$PO$_4$ in glass-distilled or deionized water, adding 10.0 mL Polysorbate™ 20 [Sigma™ P-1379 or equivalent], qs to 1000 mL, and sterile filtering using a 0.22 µm or smaller filter), and qs to 1.0 L of distilled or deionized water, stored at ambient temperature. The expiration period is 2 weeks from the date of preparation.

The ELISA diluent was PBS/0.5% BSA/0.05% Polysorbate™ 20/0.01% Thimerosal™/1 mM CaCl$_2$/1 mM MgCl$_2$. This diluent was prepared per liter as 5.0 g bovine serum albumin (Armour™ N0068 or equivalent), 50 mL 20×PBS/1.0% Polysorbate™ 20/0.2% Thimerosal™ (a mixture obtained by dissolving 160 g NaCl, 4.0 g KCl, 22.6 g Na$_2$HPO$_4$, and 4.0 g KH$_2$PO$_4$ in glass-distilled or deionized water, and adding 10.0 mL Polysorbate™ 20 [Sigma P-1379 or equivalent] and 2.0 g Thimerosal™ [Sigma T-5125 or equivalent], qs to 1000 mL), 0.1% (v/v) 1 M CaCl$_2$ (Genentech™ A3165), 0.1% (v/v) 1 M MgCl$_2$ (Genentech™ A3167), qs to 1.0 L of distilled or deionized water, and stored at 2–8° C., with the expiration period 1 month from the date of preparation.

After blocking, the plates were washed again three times with ELISA wash buffer. Soluble MAC1 (CD11b/CD18 as described by Berman et al., *J. Cell. Biochem.*, 52: 183–195 [1993]) was then captured out of a concentrate of media, conditioned by CHO cells expressing the truncated CD11b/CD18 heterodimer. After a 2-hour incubation period, the plates were washed six times with ELISA wash buffer and 100 µL of the mouse serum sample being tested or the standard containing the homologous recombinant human anti-CD18 Fab were added. The mouse serum samples were first diluted 1/10 in ELISA diluent and then a further 1/4 into sample diluent; 100 µL was taken from this initial 1/40 dilution. Sample diluent is 10% Swiss Webster Mouse serum in ELISA diluent.

Following a second 2-hour incubation, the plates were again washed six times with ELISA wash buffer and 100 µL of horseradish-peroxidase-conjugated F(ab')$_2$ directed against a human Fab was added. After a 1-hour incubation at ambient temperature, the plates were washed with ELISA wash buffer as described above and 100 µL of phosphate-buffered saline, pH 7.2, containing 2.2 mmol/L orthophenylene diamine (OPD) and 0.012% (v/v) hydrogen peroxide (H$_2$O$_2$) was added to each well. When color had fully developed, the reaction was stopped with 100 µL per well of 4.5 mol/L sulfuric acid. The absorbance of the well contents was measured at 492 nm minus 405 nm background absorbance using an automatic plate reader from SLT Labinstruments. Data were reduced by using a four-parameter, curve-fitting program based on an algorithm for least-squares estimation of non-linear parameters.

Serum concentration versus time data were analyzed utilizing a non-linear curve-fitting program and subsequent pharmacokinetics parameters were estimated. D'Argenio and Schumitzky, *ADAPT II User's Guide*, Biomedical Simulations Resource, University of Southern California, Los Angeles, Release 2, 1990.

A two-compartment model was used to characterize the serum concentration versus time data for the five groups. See Table 2 for primary model parameters and calculated pharmacokinetic parameters. The two-compartment model fit is superimposed on the data and shown in FIGS. 1A and 1B. A data listing is provided in Table 3. The volume of the central compartment approximated the plasma volume for all groups.

TABLE 2

Primary and Secondary Pharmacokinetic Model Parameter Estimates Determined After Administration of 2 mg/kg Constructs to Mice

| | Group Number | | | | |
|---|---|---|---|---|---|
| | 1 | 2 | 3 | 4 | 5 |
| Linker | Fab | Double S-S | Fab v1 | Fab v1B | Fab v2 |
| Dose (mg/kg) | 2.0 | 2.0 | 2.0 | 2.0 | 2.0 |
| $V_1/W$ (mL/kg)[a] | 44.7 | 53.9 | 51.7 | 42.3 | 49.1 |
| $K_e$ (hr$^{-1}$)[b] | 4.22 | 0.486 | 3.35 | 1.89 | 3.86 |
| $K_{cp}$ (hr$^{-1}$)[c] | 0.431 | 0.581 | 1.21 | 4.01 | 1.77 |
| $K_{pc}$ (hr$^{-1}$)[d] | 1.40 | 1.09 | 1.22 | 3.42 | 1.33 |
| CL/W (mL/hr/kg)[e] | 189 | 26 | 173 | 80 | 190 |
| $t_{1/2}\alpha$(hr)[f] | 0.14 | 0.37 | 0.14 | 0.08 | 0.11 |
| $t_{1/2}\beta$(hr) | 0.57 | 2.5 | 0.84 | 0.92 | 0.83 |
| $T_{max}$ (min)[g] | 5.0 | 5.0 | 5.0 | 5.0 | 5.0 |
| $C_{max}$ (μg/mL)[h] | 34 | 35 | 28 | 34 | 26 |
| $C_o$ (μg/mL)[i] | 39 | 46 | 39 | 44 | 39 |
| AUC/dose/W (hr*μg/mL)[j] | 9.3 | 96 | 12 | 23 | 10 |
| T (hr)[k] | 0.24 | 2.1 | 0.30 | 0.53 | 0.26 |

[a]Volume of the central compartment as calculated from the equation V = dose/$\Sigma A_i$.
[b]$K_e$ is the rate constant associated with the elimination of material from the central compartment.
[c]$K_{cp}$ is the rate constant associated with the transfer of material from the central to a peripheral compartment.
[d]$K_{pc}$ is the rate constant associated with the transfer of material from the peripheral to the central compartment.
[e]Weight-normalized serum clearance.
[f]$t_{1/2}\alpha$ and $t_{1/2}\beta$ are the initial and terminal half-lives associated with each exponential phase.
[g]Time of maximum observed concentration.
[h]Maximum observed concentrations.
[i]Zero-time concentration estimated from the disposition function as $\Sigma A_i$.
[j]Dose-normalized area under the serum concentration versus time curve.
[k]Permanence time.

TABLE 3

Data Listing: Concentration vs. time data for 2 mg/kg human anti-CD18 constructs.[a]
Concentration (μg/mL)

| Time (hours) | Group 1 | Group 2 | Group 3 | Group 4 | Group 5 |
|---|---|---|---|---|---|
| 0.083 | 28.12 | 34.28 | 26.1 | 28.16 | 25.16 |
| 0.083 | 33.89 | 34.67 | 28.38 | 33.63 | 26.39 |

TABLE 3-continued

Data Listing: Concentration vs. time data for 2 mg/kg human anti-CD18 constructs.[a]
Concentration (μg/mL)

| Time (hours) | Group 1 | Group 2 | Group 3 | Group 4 | Group 5 |
|---|---|---|---|---|---|
| 0.5 | 4.84 | 26.6 | 4.67 | 10.61 | 4.25 |
| 0.5 | 5.17 | 20.74 | 5.83 | 12.83 | 4.21 |
| 1 | 0.91 | 16.18 | 2.1 | 7.16 | 1.95 |
| 1 | 1.09 | 18.24 | 2.13 | 6.89 | 1.54 |
| 2 | 0.16 | 11.01 | 0.82 | 3.71 | 0.76 |
| 2 | 0.31 | 12 | 0.57 | 4.9 | 0.68 |
| 4 | 0.31 | 6.36 | 0.14 | 0.91 | 0.15 |
| 4 | LTS[b] | 6.78 | 0.14 | 0.67 | 0.12 |
| 8 | LTS | 1.95 | LTS | LTS | LTS |
| 8 | LTS | 1.66 | LTS | LTS | LTS |
| 12 | LTS | 0.71 | LTS | LTS | LTS |
| 12 | LTS | 0.88 | LTS | LTS | LTS |
| 16 | LTS | 0.17 | LTS | LTS | LTS |
| 16 | LTS | 0.16 | LTS | LTS | LTS |
| 20 | LTS | 0.1 | LTS | LTS | LTS |
| 20 | LTS | 0.08 | LTS | LTS | LTS |
| 24 | LTS | 0.08 | LTS | LTS | LTS |
| 24 | LTS | LTS | LTS | LTS | LTS |

[a]Concentration data represent one sample per mouse.
[b]LTS = Less than the sensitivity of the assay (0.13 μg/ml for groups 1 and 3–5; 0.06 μg/ml for group 2).

Results

Figure 1B:
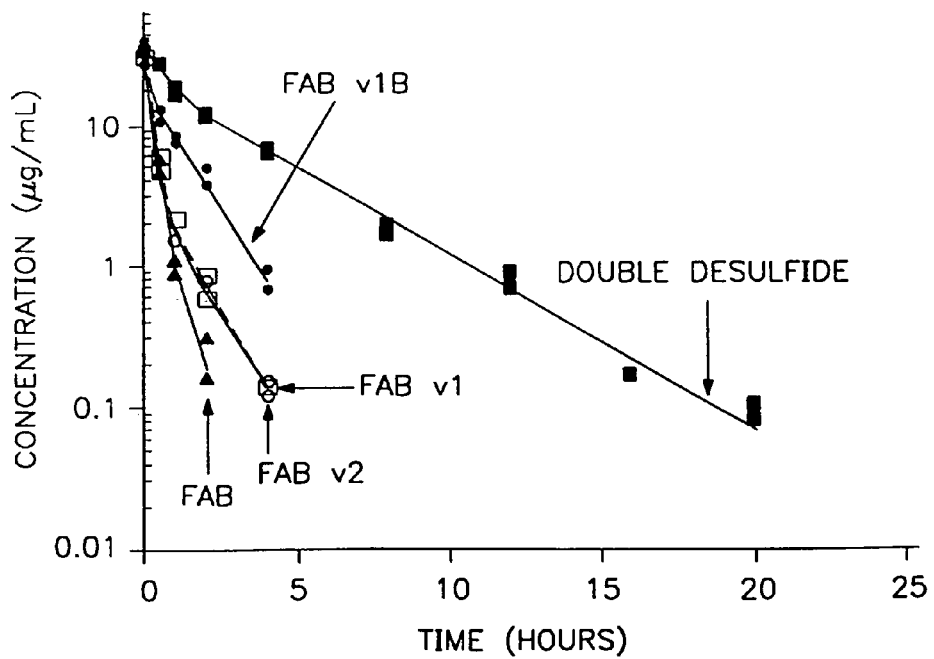

The data are shown in FIGS. 1A and 1B, where FIG. 1A shows the pharmacokinetics of all five constructs over a time period of 0 to 5 hours, and FIG. 1B shows the pharmacokinetics of all five constructs over a time period of 0 to 25 hours. The initial (or α-phase) half-lives varied as did the terminal (β-phase) half-lives. The Fab v1B variant had a clearance of 80 mL/hr/kg, which is about three-fold higher than that of the double-disulfide (Fab')$_2$. The Fab v1, Fab, and Fab v2 had approximately 3-fold greater clearance over the Fab v1B and about 6-fold greater clearance over the double-disulfide (Fab')$_2$ (173, 189, and 190 mL/hr/kg, respectively).

The effective molecular weight of the original Fab was 49 kD, and its clearance was 189 mL/hr/kg.

The Fab versions 1, 1B, and 2 all have molecular weights similar to that of the original Fab, yet version 1B was cleared from the serum 2-fold more slowly. Thus, alterations of the amino acid sequence in the Fab constant domain affect clearance. The effect seen on beta-phase half-life shows that with the two least-successful variants 1 and 2, there was a detectable effect that was not sufficient to increase significantly overall permanence time.

What is claimed is:

1. A nucleic acid encoding a modified polypeptide with an improved in vivo half-life, said modified polypeptide comprising an Ig constant domain or Ig-like constant domain and a salvage receptor binding epitope within said Ig constant domain or Ig-like constant domain, wherein said epitope is absent from the unmodified polypeptide, wherein said salvage receptor binding epitope is taken from one loop of the CH$_2$ domain of an Fc region of an Ig molecule and wherein said polypeptide in modified form does not comprise an intact CH$_2$ domain or an intact Fc region.

2. The nucleic acid of claim 1 wherein the Ig domain or Ig-like domain comprises a CH$_1$ domain.

3. The nucleic acid of claim 1 wherein the unmodified polypeptide is a Fab, a (Fab')$_2$, a diabody, a Fv fragment, a single chain Fv fragment, or a receptor.

4. The nucleic acid of claim 3 wherein the unmodified polypeptide is an anti-CD18 Fab or an anti-CD18 F(ab')$_2$.

5. The nucleic acid of claim 4 wherein the antiCD18 Fab or antiCD18 F(ab')$_2$ is human or humanized.

6. The nucleic acid of claim 1 wherein said salvage receptor binding epitope comprises amino acids from 1 through 11 of SEQ ID NO:3.

7. The nucleic acid of claim 1, wherein the unmodified polypeptide is selected from the group consisting of an antibody directed against CD11a or CD18 or both, a soluble form of ICAM-1, an antibody to ICAM-1, and fragments thereof.

8. A vector comprising the nucleic acid of any one of claims 1, 2–6, and 7.

9. A host cell comprising the nucleic acid of any one of claims 1, 2–6, 7, and 8.

10. A method for producing a modified polypeptide comprising culturing the host cell according to claim 9 in a culture medium and recovering the modified polypeptide.

11. The nucleic acid of claim 1, wherein the unmodified polypeptide is a growth hormone or a nerve growth factor.

* * * * *